United States Patent [19]
Miwa et al.

[11] Patent Number: 5,515,727
[45] Date of Patent: May 14, 1996

[54] ULTRASOUND SIGNAL PROCESSOR

[75] Inventors: Yuichi Miwa, Ann Arbor, Mich.; Kageyoshi Katakura, Tokyo, Japan; Ryuichi Shinomura, Higashimatsuyama, Japan; Hiroshi Masuzawa, Hachioji, Japan; Yutaka Sato, Kashiwa, Japan; Shizuo Ishikawa, Kanagawa, Japan

[73] Assignee: Hitachi Medical Corporation, Tokyo, Japan

[21] Appl. No.: 124,555

[22] Filed: Sep. 22, 1993

[30] Foreign Application Priority Data

Sep. 22, 1992 [JP] Japan ................... 4-252576
Mar. 5, 1993 [JP] Japan ................... 5-045265

[51] Int. Cl.$^6$ ........................... G01N 29/00
[52] U.S. Cl. ........................... 73/602; 73/633
[58] Field of Search ............... 73/587, 596, 598, 73/600, 601, 570, 602, 618, 619, 633

[56] References Cited

U.S. PATENT DOCUMENTS

| | | | |
|---|---|---|---|
| 4,226,121 | 10/1980 | Knospler | 73/602 |
| 4,307,616 | 12/1981 | Vasile | 73/643 |
| 4,841,489 | 6/1989 | Ozaki et al. | 73/633 |
| 5,005,419 | 4/1991 | O'Donnell | 73/626 |
| 5,027,821 | 7/1991 | Hirama et al. | 73/625 |

OTHER PUBLICATIONS

Japanese Patent Publication No.60–51068.
U.S. Pat. No. 4,140,022.

*Primary Examiner*—Richard Chilcot
*Assistant Examiner*—Max Noori
*Attorney, Agent, or Firm*—Antonelli, Terry, Stout & Kraus

[57] ABSTRACT

An ultrasound signal processor has a receiving signal digitizing circuit, waveform conversion circuit for mixing a produced digital signal by a reference signal, a cumulation circuit for performing a cumulation processing of a series of converted signals, a delay circuit subject to the cumulation processing, and a circuit for adding delayed signals, whereby the frequency of the receiving signal is shifted to a lower frequency and thereafter subjected to a cumulation processing which perform over-sampling technique so that the accuracy of an analog to digital conversion can be improved drastically. The ultrasound signal processor further has a circuit for converting a receiving signal into a low frequency signal by analog-mixing and a circuit for passing a low frequency component of the analog-converted signal, whereby a higher frequency receiving signal can be digitized even if the digitizing circuit has a insufficient sampling rate.

15 Claims, 17 Drawing Sheets

FIG. 7
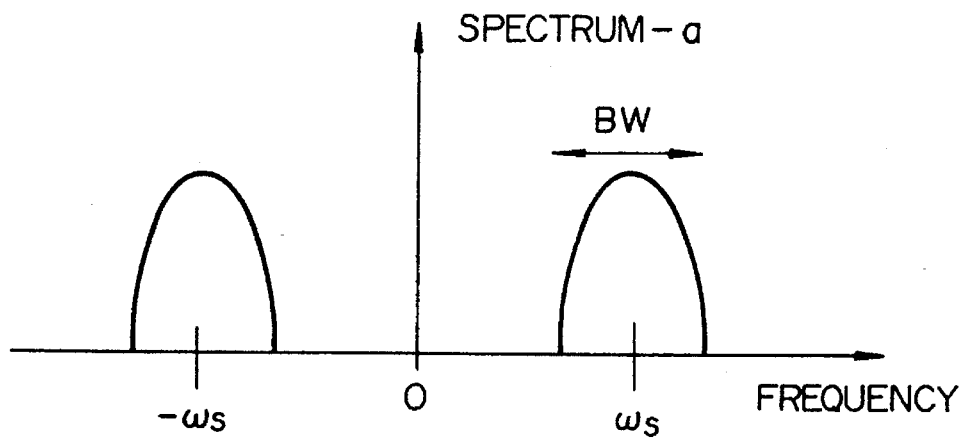
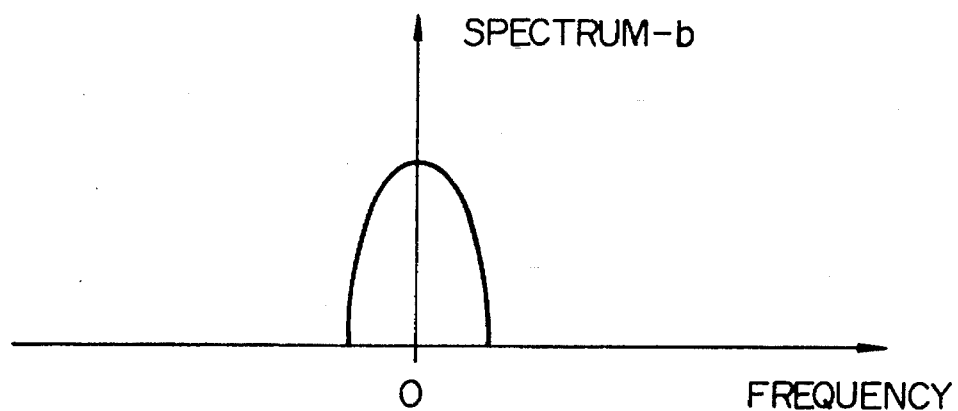
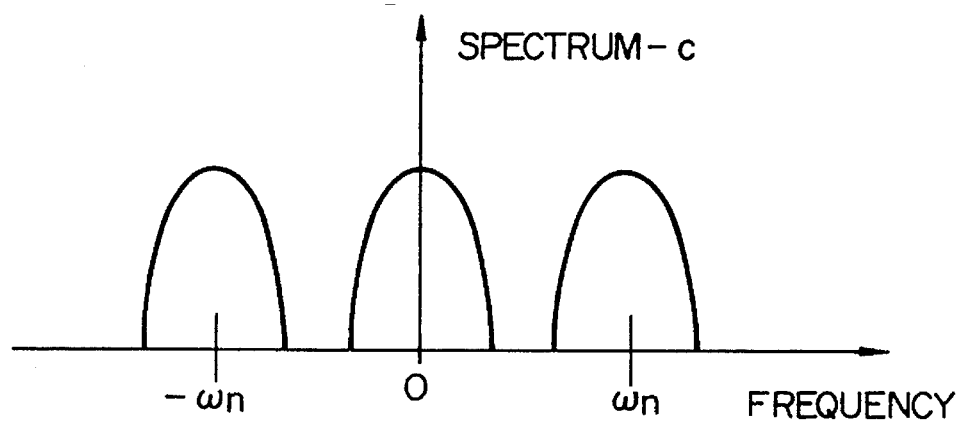
$\omega n = ADFQ / COUNT$

FIG. 9
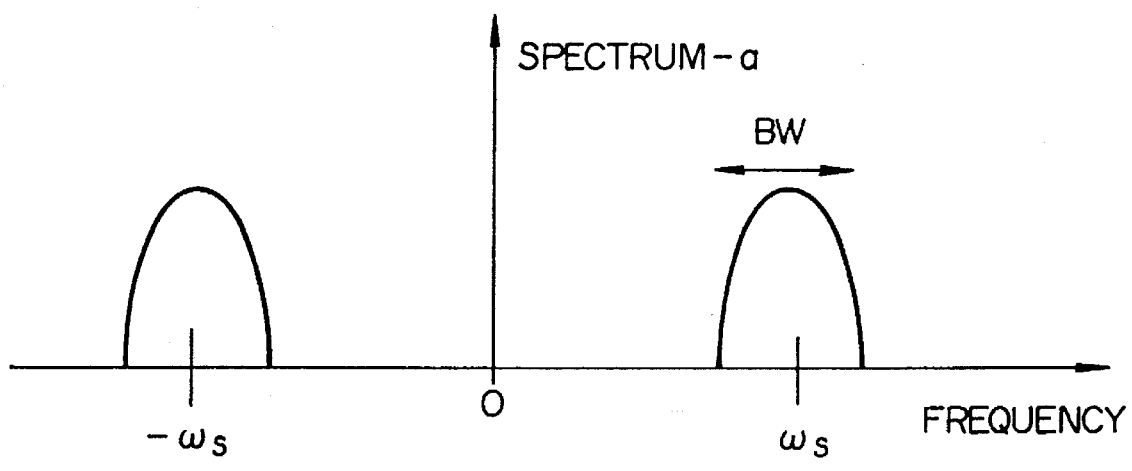
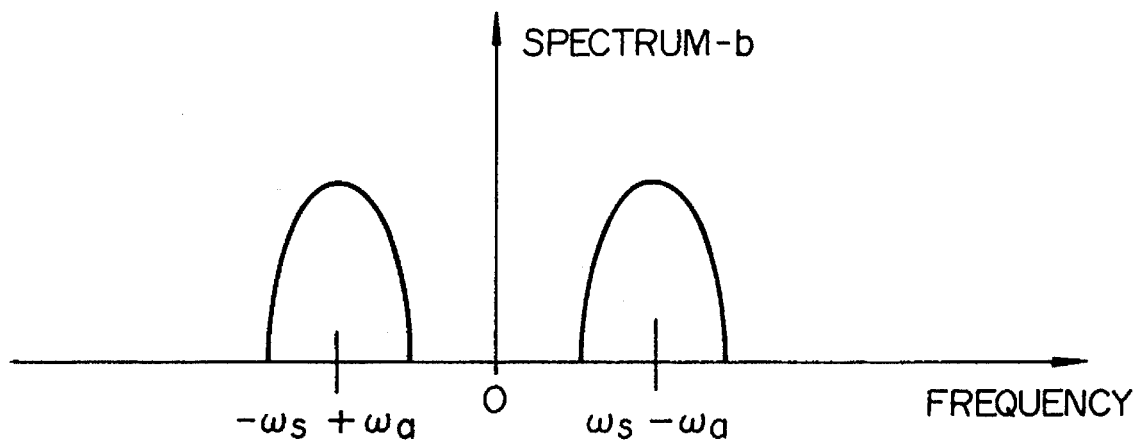

ULTRASOUND SIGNAL PROCESSOR

BACKGROUND OF THE INVENTION

The present invention relates to signal processing either in an apparatus for performing non-destructive testing of a material object or in an ultrasound apparatus used for medical diagnosis and more particularly to an ultrasound signal processor suitable for digitization.

A conventional ultrasound receiver is comprised of analog delay circuits and adders and it radiates ultrasound to an object to be tested, then receives an echo from the object to be tested by means of a receiving element array and adjusts the delay time between receiving signals to change the direction of a receiving beam. The incident direction of the ultrasound is made to be coincident with the direction of formation of the receiving beam, and outputs of respective array receiving elements are made to be in phase and added together to thereby obtain a total output which is large. Receiving signals from an object other than the target, which are received by the respective array receiving elements, are out of phase from each other and consequently cancelled out to thereby produce a total output which is suppressed. Since signals received by a plurality of receiving elements are made to be in phase and added together in this manner to improve resolution, accuracy of the delay time of analog delay circuits must be increased, giving rise to problems of complicated apparatus configuration and high cost. Accordingly, an apparatus has been proposed which simplifies the apparatus configuration and which is mainly constructed of analog circuits not required to have high delay time accuracy. This is based on ultrasound beamforming or so-called beat-down in which the center frequency of a receiving signal is shifted and delayed and thereafter subjected to an adding processing. More specifically, in the beamformer of ultrasound signals, a signal from an ultrasound receiving element is mixed with a reference signal, precisely controlled with respect to time, so as to be converted into a low frequency signal, wherein the low frequency signal component is delayed by means of a delay circuit. Signals from the respective elements which are thus produced are finally added together. A configuration using this method is shown in FIG. 2.

In FIG. 2, reference numeral 23 designates a transducer of ultrasound, 14 denotes an analog mixer, 6 indicates an analog delay circuit whose delay time is settable, 2 represents an analog adder, 18 designates an analog reference signal generator, and 8 denotes a control circuit for analog delay. Where t represents time, a transmitting signal s(t) having a center frequency $\omega_s$ can be approximated by $$S(t) = A_0(t)\{exp(j\omega_s t) + exp(-j\omega_s t)\} \quad (1)$$

wherein $A_0(t)$ indicates an envelope form of the transmitting signal and j is imaginary unit. A receiving signal $f_n(t)$ of a targeted echo signal generated from this transmitting signal and received by an n-th array receiving element is given by $$\begin{aligned}f_n(t) &= k_n s(t - \tau_n) \quad (2)\\ &= k_n A_0(t)\{exp(j\omega_s t) + exp(-j\omega_s t)\}\\ &= A_n(t - \tau_n)[exp\{j\omega_s(t - \tau_n)\} + exp\{-j\omega_s(t - \tau_n)\}]\\ &= A_n(t - \tau_n)[exp\{j(\omega_s t - \phi_n)\} + exp\{-j(\omega_s t - \phi_n)\}]\end{aligned}$$

where $\tau_n$ is propagation time of the ultrasound. Here $A_n = k_n A_0$ and $k_n$ is a coefficient determined by a propagation distance of the echo. Multiplication of this signal by a reference signal $h_n(t)$ generated from the analog reference signal generator 18 is carried out by the analog mixer 14. For simplification, it is now assumed that $h_n(t)$ is a signal having the same frequency as a carrier of the receiving signal, and $h_n(t)$ is given by $$h_n(t) = exp\{-j(\omega_s t - \phi_n)\} \quad (3)$$

when a phase term $\phi_n$ is taken into consideration. A multiplication result $g_n(t)$ is $$\begin{aligned}g_n(t) &= f_n(t) h_n(t) \quad (4)\\ &= A_n(t - \tau_n)[1 + exp\{-2j(\omega_s t - \phi_n)\}].\end{aligned}$$

When only a carrier component which is direct current is considered, the multiplication result is expressed by $G_n(t)$ which is $$G_n(t) = A_n(t - \tau_n) \quad (5).$$

This waveform is delayed by a time of $\tau_0 - \tau_n$ by means of the analog delay circuit 6 to provide a signal $V_n(t)$ which is $$\begin{aligned}V_n(t) &= G_n(t - \tau_n - (\tau_0 - \tau_n)) \quad (6)\\ &= A_n(t - \tau_0)\end{aligned}$$

where $\tau_0$ is a constant determined by the analog delay circuit 6. As will be seen from the above, signal $V_n(t)$ results from time shift of $A_n(t)$, and $A_n(t)$ is constant times as large as the envelope $A_0$ of the transmitting signal. Therefore the signal $V_n(t)$ has a common waveform whose amplitude scale depends on n. Consequently, in a final result which is obtained by adding thus processed signals by means of the analog adder 2 and which is expressed by $$Y(t) = \sum_{n=1}^{N} V_n(t), \quad (7)$$

respective signals are in phase with each other and the sum Y(t) grows greatly. On the other hand, in an echo coming from a direction other than the targeted direction, respective signals have phases which are different from $\phi_n$ in equation (3) and a phase term remains in equation (5). This causes interference due to the phase difference occurring during addition pursuant to equation (7) and thus the sum Y(t) damps. Based on the operational principle described above, receiving signals from the targeted direction can be selected. For example, Japanese Patent Publication No. 51068/1985 and U.S. Pat. No. 4,140,022 are relevant to this type of apparatus. The configuration shown in FIG. 2 is typically realized with analog circuits but in order to improve accuracy of beamforming and further enhance the quality of the apparatus, it may preferably be realized with digitized operation units.

Conceivably, the conventional apparatus constructed of analog circuits may be simply digitized with, for example, an apparatus constructed as shown in FIG. 3. In FIG. 3, an analog to digital converter 5 is used and the analog mixer 14, analog delay circuit 6, analog adder 2, analog reference signal generator 18 and control circuit 8 for analog delay shown in FIG. 2 are modified for digitization to provide a digital mixer 15, a digital delay circuit 7, a digital adder 3, a digital reference signal generator 19 and a control circuit 9 for digital delay, respectively, which are used in FIG. 3. In this configuration, the analog to digital (A/D) converter is required to have many bits, for example, 10 bits or more to ensure amplitude accuracy in ordinary applications of ultrasound. Under the circumstances, a configuration is conceivable wherein a so-called over-sampling technique using known fast sampling and cumulation of signals in combination is applied to increase the effective number of bits. For example, in an example of configuration of FIG. 4, a digital adder 4 for cumulation adapted to calculate the sum of a plurality of signals is arranged between the analog to digital converter 5 and digital mixer 15 shown in FIG. 3. The effect of this over-sampling technique depends on the number of cumulating operations but the ultrasound signal has a waveform as shown in FIG. 5, with the result that the time length for permitting cumulation within an amplitude change of Δ or less is limited to $T_0$ or less and a remarkable improvement in accuracy cannot be expected. In FIG. 5, A(t) represents an envelope having the same form as that of the envelope of the transmitting signal s(t) and this waveform is a typical example in the conventional ultrasonic apparatus.

In the prior art described above, when materializing a highly accurate digital beamforming processing, a problem arose in simplifying the analog to digital converter. Further, it was difficult to improve both the amplitude accuracy and the sampling frequency of the analog to digital converter in compliance with a receiving signal having a high center frequency. Further, there arose a problem that a sampling frequency of the analog to digital converter not sufficiently higher than easily twice the upper limit frequency of a receiving signal component, could not be dealt with.

SUMMARY OF THE INVENTION

An object of the present invention is to solve the above problems and to provide an ultrasound signal processor which can remarkably improve the accuracy of analog to digital conversion, especially for a receiving signal having a high center frequency, and can be simplified in configuration so as to be suited for cost reduction.

To accomplish the above object, a signal processor of the present invention comprises a circuit for digitizing a receiving signal, a circuit for mixing a resulting digital signal with a reference signal of a predetermined frequency to convert it into a low frequency signal, and a circuit for performing a cumulation processing of converted signals in series, whereby the cumulation processing is carried out after the frequency of the receiving signal is shifted to a lower frequency.

An ultrasound signal processor of the present invention comprises a digitizing circuit for digitizing a receiving signal, a waveform conversion circuit for converting a signal waveform by multiplying a resulting digital signal by a reference signal of a predetermined frequency, a cumulation circuit for performing a cumulation processing of converted signals in series, a delay circuit for delaying a signal subjected to the cumulation processing, and an adder circuit for adding delayed signals, whereby the cumulation processing is carried out after the frequency of the receiving signal is shifted to a lower frequency by utilizing characteristics of ultrasound signals. A plurality of groups of the waveform conversion circuits may be provided or a circuit for storing signals subjected to the cumulation processing may be provided.

To accomplish the above object, the ultrasound signal processor of the present invention further comprises a circuit for converting a receiving signal into a low frequency signal by analog-mixing the receiving signal with an analog reference signal of a predetermined frequency, and a filter circuit for passing a low frequency component of an analog-converted signal, whereby the frequency of the receiving signal is first shifted to a lower frequency through the analog signal processing, a resulting low frequency signal is digitized, the frequency of the resulting digital signals then shifted further to a lower frequency through digital signal processing and thereafter resulting low frequency signals are subjected to a cumulation processing. An envelope of a transmitting signal can be reconstructed by limiting the number of cumulation operations during the cumulation processing of the digital converted signals and the frequency of the reference signal used during the analog waveform conversion.

In the present invention, the over-sampling technique is used for the digital processing of ultrasound signals and the cumulation processing is carried out after the frequency is shifted to a lower frequency, in order that even with a simplified configuration, the effective accuracy of analog to digital conversion can be improved greatly. Especially, by using the over-sampling technique in which an ultrasound signal having a high center frequency is shifted to a lower frequency through an analog signal processing, the frequency is further shifted to a lower frequency through a digital signal processing and thereafter a cumulation processing is carried out, the effective accuracy of analog to digital conversion can be improved greatly with a simplified configuration even for the ultrasound signal having a high center frequency.

In accordance with the present invention, by performing a cumulation processing after an ultrasound signal is shifted to a lower frequency, the over-sampling processing can act effectively to drastically improve the effective accuracy of analog to digital conversion. Through this, the configuration of the analog to digital converter in a digital type ultrasound apparatus operable at a high center frequency can be simplified, thus contributing to cost reduction. Especially, by shifting an ultrasound signal having a high center frequency to a lower frequency, digitizing a resulting low frequency signal, further shifting a resulting digital signal to a lower frequency through a digital processing, and cumulating low frequency signals, the over-sampling processing can act effectively to drastically improve the accuracy of analog to digital conversion.

BRIEF DESCRIPTION OF THE DRAWINGS

FIG. 7 is a graph for explaining the beat-down of a receiving signal in the present invention.

FIG. 9 is a graph showing how spectra of a receiving signal change due to analog mixing.

DESCRIPTION OF THE PREFERRED EMBODIMENTS

Embodiments of the present invention will now be described with reference to the accompanying drawings.

First Embodiment

Figure 1:
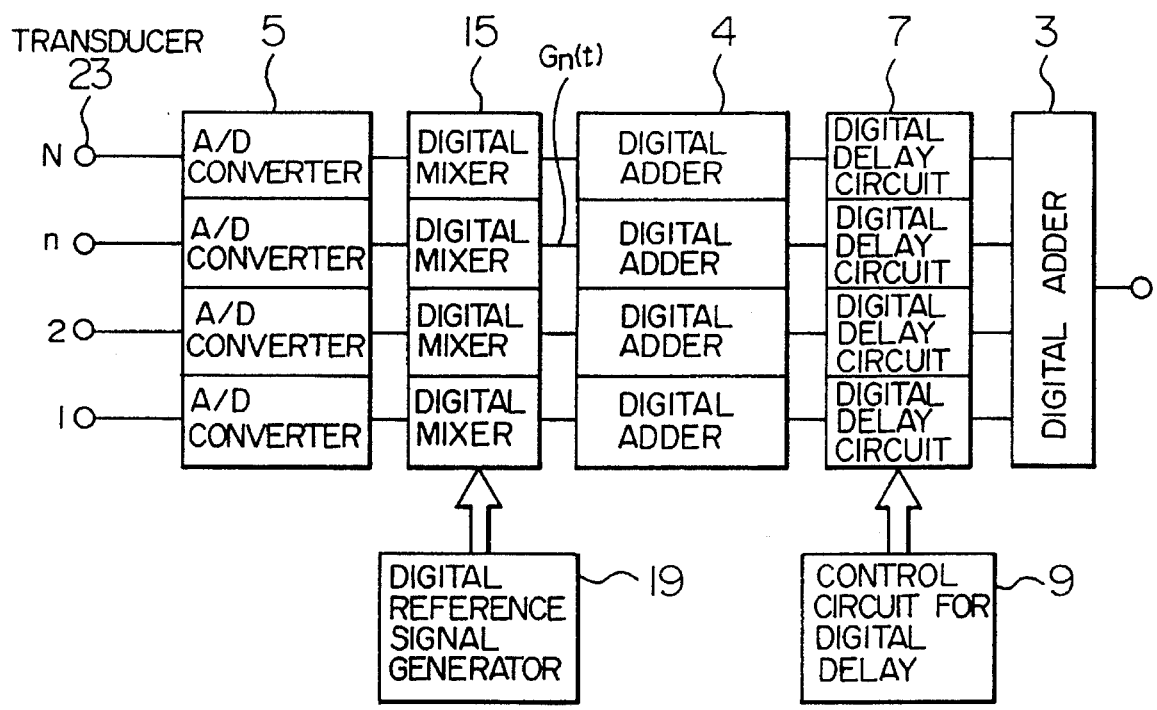
FIG. 1 is a diagram showing a configuration of an ultrasound signal processor according to a first embodiment of the present invention.
Figure 2:
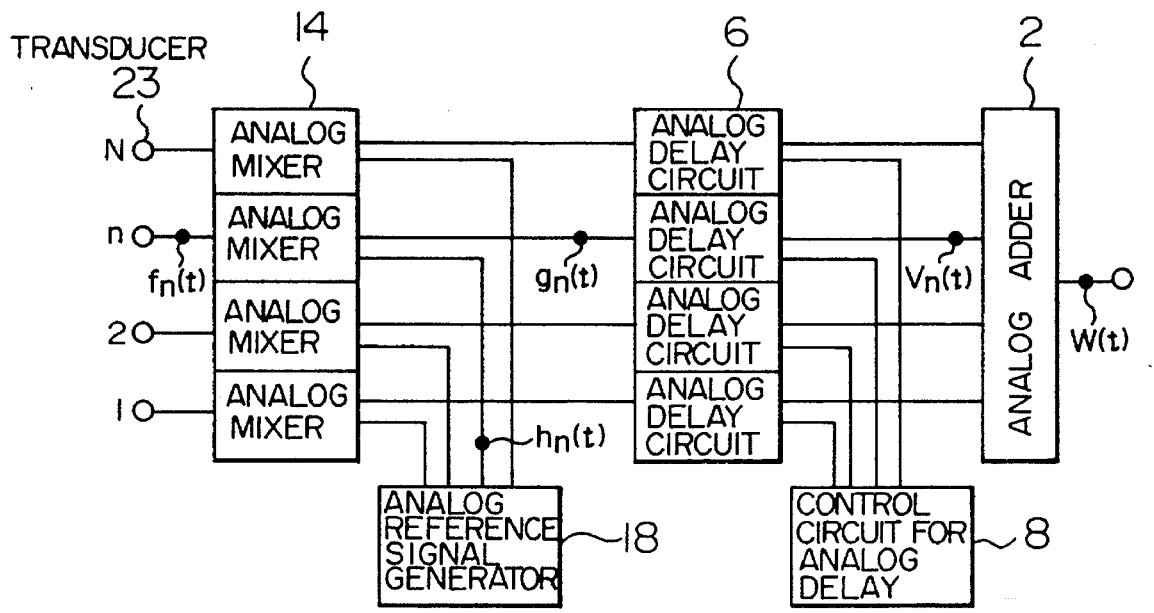
FIG. 2 is a diagram showing a configuration of a prior art analog type ultrasound signal processor to which the beat-down beamforming is applied.
Figure 3:
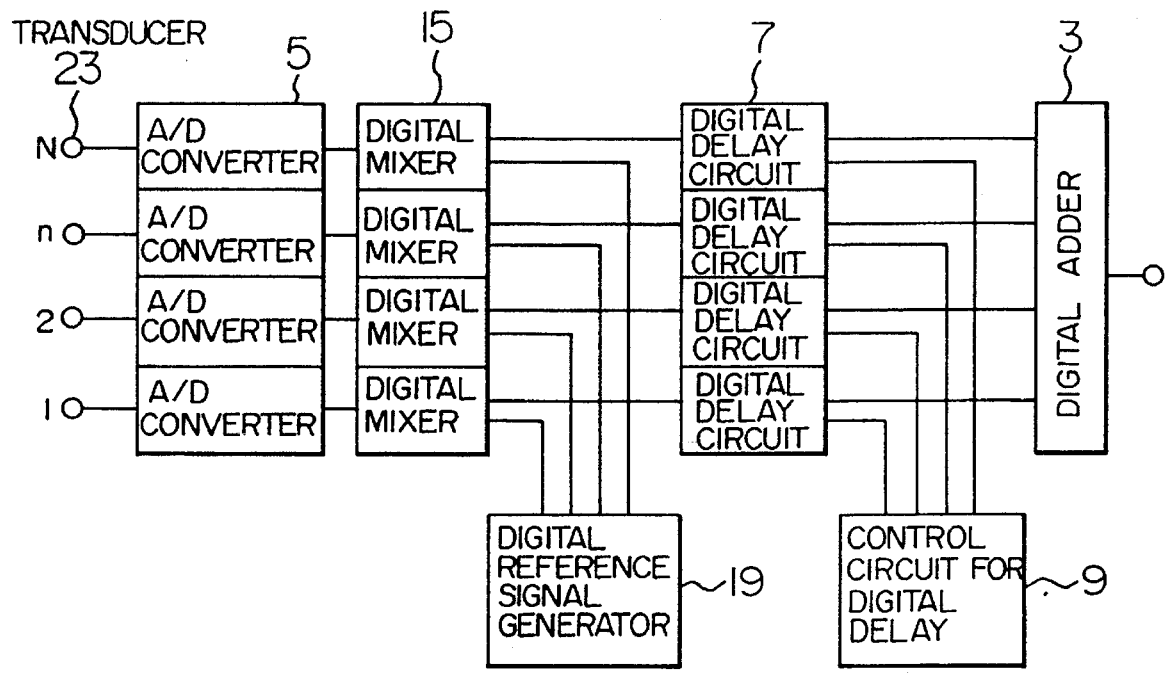
FIG. 3 is a diagram showing a configuration wherein the ultrasound signal processor of FIG. 2 is digitized.
Figure 4:
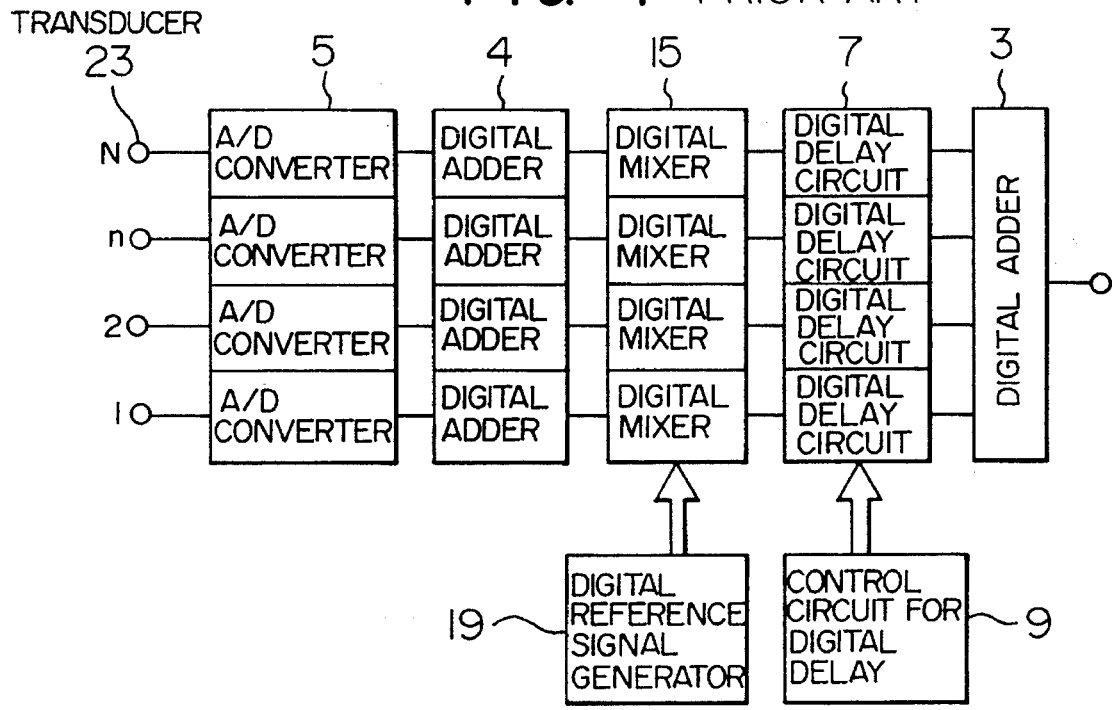
FIG. 4 is a diagram showing a configuration wherein the over-sampling technique is applied to the ultrasound receiver of FIG. 3.
Figure 5:
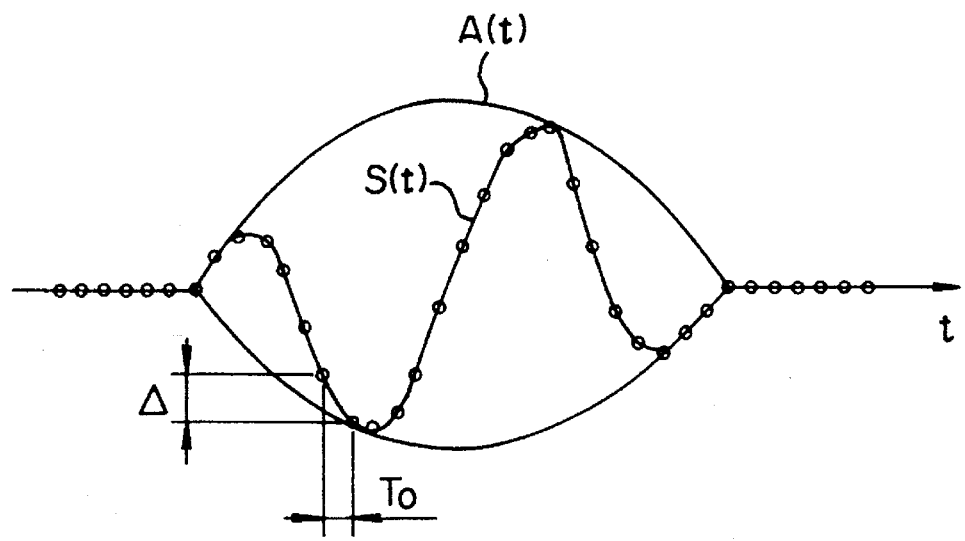
FIG. 5 is a diagram showing an ultrasound waveform obtained with the prior art ultrasound signal processor.
Figure 6:
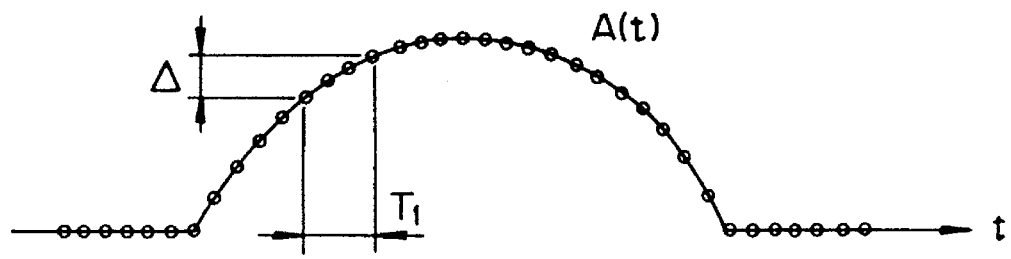
FIG. 6 is a diagram showing an ultrasound waveform obtained with the ultrasound signal processor according to the first embodiment of the present invention.

FIG. 1 is a diagram showing a configuration of an ultrasound signal processor for realization of accurate digital beamforming processing according to a first embodiment of the present invention. In FIG. 1, a digital adder 4 for cumulation adapted to calculate the sum of signals in series is interposed between the digital mixer 15 and digital delay circuit 7 shown in FIG. 3. In this case, signals to be cumulated are of low frequency component $G_n(t)$ delivered out of the digital mixer 15, that is, of an envelope form corresponding to $A_n(t-\tau_n)$ pursuant to equation (5). Therefore, as shown in FIG. 6, cumulation processing can proceed for a much longer time $T_1$ than $T_0$ shown in FIG. 5. The number of cumulating operations in the digital adder 4 for cumulation will be described. A spectrum as shown in FIG. 7 is an amplitude spectrum of s(t) and BW represents a band width of envelope A(t). Practically, because of sampling at the analog to digital converter, the spectrum a undergoes aliasing at a period of a sampling frequency of the analog to digital converter, but here, on the assumption that the sampling frequency of the analog to digital converter is sufficiently larger than $\omega_s$, spectrum aliasing is omitted. Since the spectrum a in FIG. 7 is subjected to multiplication by $\exp(-j\omega_s t)$ at the digital mixer 15 and to extraction of a low frequency component at the digital adder 4 for cumulation, an envelope spectrum centered at the zero frequency as shown at spectrum b in FIG. 7 develops as a spectrum of the adder output. In this phase, signal sampling frequency is reduced to (ADFQ/COUNT), where ADFQ is the sampling frequency of the analog to digital converter 5 and COUNT is the number of cumulation operations in the digital adder 4 for cumulation. Since the effect of improving S/N in the over-sampling technique becomes remarkable as the number of cumulation operations in the digital adder 4 for cumulation increases, aliasing at a period of the above (ADFQ/COUNT) cannot be neglected and there results a spectrum c as shown in FIG. 7. In order to completely reconstruct the envelope, duplication of the spectrum aliasing must be avoided and hence $$\text{COUNT} \leq (\text{ADFQ/BW}) \tag{8}$$

must stand. In this manner, a condition imposed on the number of cumulation operations is determined automatically from the band width of the envelope and the sampling frequency of the analog to digital converter. However, when improvement on S/N due to the number of cumulation operations is desired to predominate over slight overlapping of spectrum aliasing, equation (8) need not be satisfied. Returning to FIG. 1, the sampling theorem prescribes that the sampling frequency of the analog to digital converter 5 should be twice or more an upper limit frequency necessary for a frequency band of the transmitting signal s(t). On the assumption that the upper limit frequency is about 5 MHz, the sampling frequency of the analog to digital converter 5 may be 10 MHz or more and the over-sampling can be effected satisfactorily by using an analog to digital converter 5 of, for example, 25 MHz which is easily available at present. In addition, when the analog to digital converter 5 operates at 25 MHz, the operation frequency of the digital mixer 15 is also 25 MHz, thus permitting easy integration. Accordingly, the configuration exemplified in FIG. 1 is said to be very suitable for highly accurate digital beamforming processing. But when the aforementioned upper limit frequency is set to 15 MHz, the analog to digital converter 5 needs a sampling frequency which is at least 30 MHz and for the over-sampling, an analog to digital (A/D) converter of very high operation frequency (assumed to be 2.5 times larger than 30 MHz, amounting up to 75 MHz) is needed which is expensive and has high power consumption. The operating frequency of the digital mixer 15 also increases and integration is difficult to achieve. As will be seen from the above, the configuration example shown in FIG. 1 has difficulties in dealing with a high frequency ultrasound signal.

Second Embodiment

Figure 8:
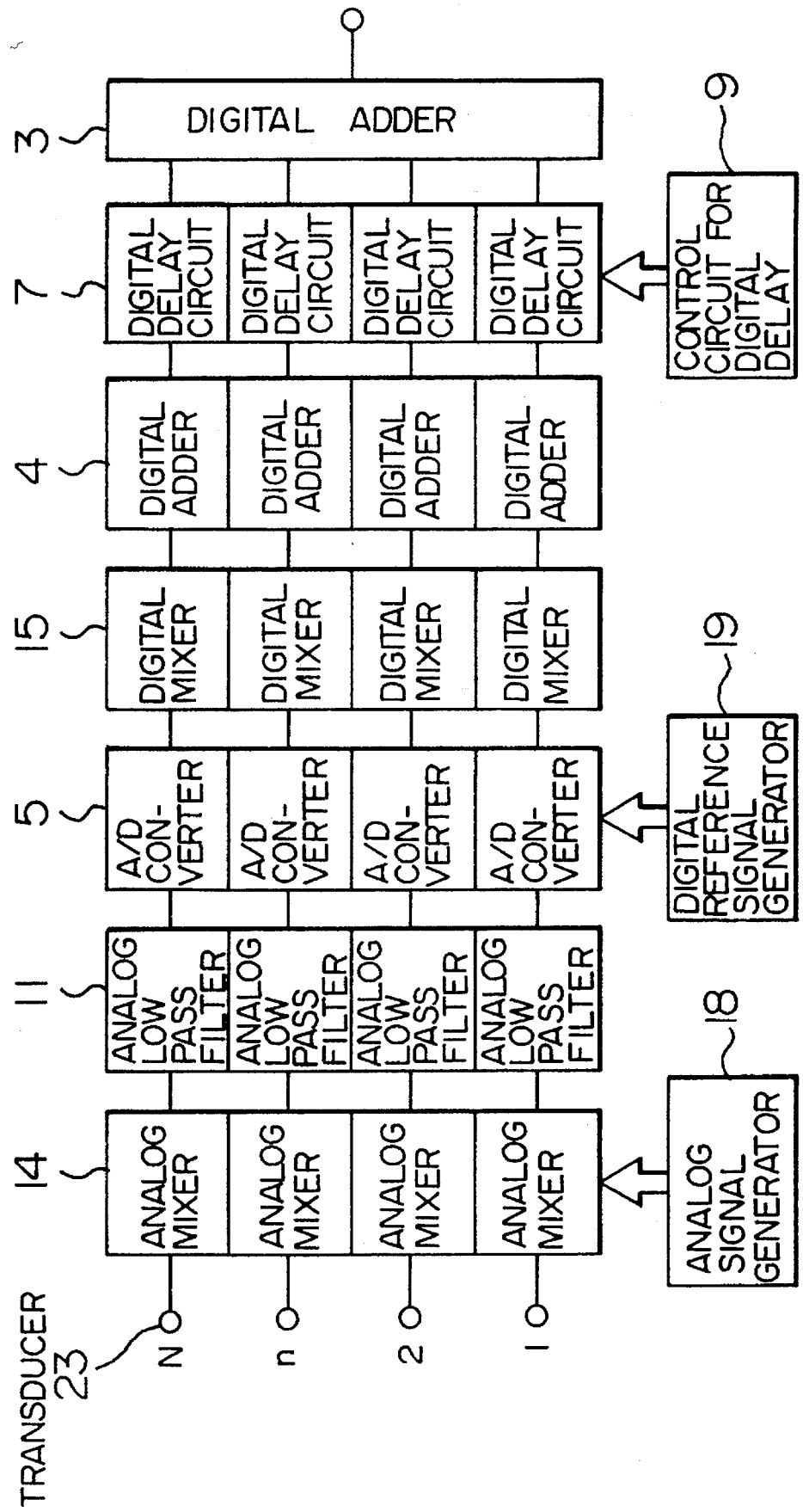
FIG. 8 is a diagram showing a configuration of an ultrasound signal processor according to a second embodiment of the present invention.

FIG. 8 is a diagram showing a configuration of an ultrasound signal processor according to a second embodiment of the present invention. In FIG. 8, reference numeral 14 designates an analog mixer, 11 denotes an analog low pass filter, 5 represents an analog to digital converter, 15 designates a digital mixer, 4 dentoes a digital adder for cumulation, 7 designates a digital delay circuit and 3 denotes a digital adder. Reference numeral 18 designates an analog reference signal generator used when a receiving signal is subjected to analog mixing at the analog mixer 14, 19 designates a digital reference signal generator used when a receiving signal having undergone analog to digital conversion is subjected to digital mixing at the digital mixer 15, and 9 designates a control circuit for digital delay. A receiving signal at an n-th element is given by $$f_n(t) = A_n(t-\tau_n)[exp\{j(\omega_s t - \phi_n)\} + exp\{-j(\omega_s t - \phi_n)\}] \quad (9)$$

Real number expression of equation (9) is $$f_n(t) = 2A_n(t-\tau_n)\cos(\omega_s t - \phi_n) \quad (10)$$

Multiplication of the signal of equation (10) by a reference signal $m_n(t)$ generated from the analog reference signal generator 18 is carried out at the analog mixer 14. For simplicity, on the assumption that the phase of $m_n(t)$ is 0(zero) at t=0, there results $$m_n(t) = \cos(\omega_a t) \quad (11)$$

and the multiplication at the analog mixer 14 becomes multiplication of real number. Accordingly, a multiplication result $O_n(t)$ is given by $$O_n(t) = f_n(t)m_n(t) = A_n(t-\tau_n)[\cos\{(\omega_s+\omega_a)t-\phi_n\} + \cos\{(\omega_s-\omega_a)t-\phi_n\}] \quad (12)$$

and this is passed through the analog low pass filter 11 to provide $$O_n(t) = A_n(t-\tau_n)\cos\{(\omega_s-\omega_a)t-\phi_n\} \quad (13),$$

which is returned to complex expression to provide $$O_n(t) = A_n(t-\tau_n)[exp\{j((\omega_s-\omega_a)t-\phi_n)\} + exp\{-j((\omega_s-\omega_a)t-\phi_n)\}]. \quad (14)$$

In equation (14), $\omega_s$ in equation (9) is substituted by $\omega_s-\omega_a$, indicating that the center frequency of the receiving signal is decreased from $\omega_s$ to $\omega_s-\omega_a$ and when $\omega_s$ is large, components following the analog to digital converter 5 can be constructed easily. Then, by newly taking $\omega_s-\omega_a$ for $\omega_s$, signal processings after equation (14) become identical to those explained with reference to equations (3) and (7). The reference signal from the analog reference signal generator 18 may otherwise be defined by $$m_n(t) = \cos(\omega_a t - \phi_n) \quad (15).$$

In this case, the output of the analog low pass filter 11 is given by $$O_n(t) = A_n(t-\tau_n)\cos\{(\omega_s-\omega_a)t\} \quad (16).$$

As described above, by newly taking $\omega_s-\omega_a$ for $\omega_s$, multiplication at the digital mixer 15 is defined as $$h_n(t) = exp(-j\omega_s t) \quad (17),$$

which is common to the respective elements.

The frequency of the reference signal participating in the multiplication in the analog mixer 14 will be described. The spectrum of s(t) is assumed to be a spectrum a as shown in FIG. 9. Like FIG. 7, spectrum aliasing at a period of the sampling frequency of the analog to digital converter is omitted. BW represents a band width of an envelope. Since in the analog mixer 14 the multiplication by $\cos(\omega_a t)$ is effected, the output spectrum of the analog low pass filter 11 becomes a spectrum b as shown in FIG. 9. If in this case two envelope spectra lying at positive and negative frequencies overlap, the envelope cannot be reconstructed in the ensuing operation. Accordingly, in order to completely reconstruct the envelope, a condition as expressed by $$\omega_a \leq \omega_s - (BW/2) \quad (18)$$

is needed. In this case, too, if beat-down of the center frequency of s(t) has precedence over slight overlapping of the envelope spectra, equation (18) need not be satisfied.

The following description will proceed on the assumption that the center frequency $\omega_s-\omega_a$ of the receiving signal shifted to a lower frequency by analog beat-down is taken for new $\omega_s$. The $h_n(t)$ is defined as $$h_n(t) = exp\{-j(\omega_s t - \phi_n)\} \quad (19)$$

in equation (3), but it may not be a complex variable function but may be a real variable function. In such a case, $h_n(t)$ is given by $$h_n(t) = \cos(\omega_s t - \phi_n) \quad (20).$$

A multiplication result $g_n(t)$ is given by $$\begin{aligned} g_n(t) &= f_n(t)h_n(t) \\ &= A_n(t-\tau_n)[1 + \cos\{2(\omega_s t - \phi_n)\}]. \end{aligned} \quad (21)$$

When only the low frequency component is taken into consideration, $G_n(t)$ is given by equation (5) as in the preceding description.

A case where $\omega_s$ and $\tau_n$ are unknown and approximate value $\omega_m$ of $\omega$ and the time difference between the receiving signal of each element and a standard receiving signal are known will now be described. Thus, when the standard receiving signal is $f_1(t)$, $\tau_n-\tau_1$ is known. In this case, $h_n(t)$ is given by $$h_n(t) = exp[-j\{\omega_m t - (\omega_m+\omega_a)(\tau_n-\tau_1)\}] \quad (22).$$

The low frequency component of multiplication result $g_n(t)$ is expressed by $$G_n(t) = A_n(t-\tau_n)exp[+j\{(\omega_s-\omega_m)(t-\tau_n)-(\omega_m+\omega_a)\tau_1\}] \quad (23).$$

When a signal obtained by delaying equation (23) by $\tau_1-\tau_n$ is $V_n(t)$, there results $$\begin{aligned} V_n(t) &= g_n(t+\tau_n-\tau_1) \\ &= A_n(t-\tau_1)exp[+j\{(\omega_s-\omega_m)(t-\tau_1)-(\omega_m+\omega_a)\tau_1\}] \\ &= A_n(t-\tau_1)exp[+j\{(\omega_s-\omega_m)t-\phi_1\}], \end{aligned} \quad (24)$$

whose amplitude is proportional to a common waveform ($A_0(t)$), where $\phi_1 = -(\omega_s+\omega_a)\tau_1$. Since equation (24) is of complex number, the envelope can be obtained in terms of an absolute value of the complex number. A real variable function form of equation (22) is $$h_n(t) = \cos\{\omega_m t - (\omega_m+\omega_a)(\tau_n-\tau_1)\} \quad (25).$$

Then, $V_n(t)$ becomes $$V_n(t) = A_n(t-\tau_1)\cos\{(\omega_s-\omega_m)t-\phi_1\} \quad (26).$$

In equation (26), the envelope cannot be determined when $\omega_s$ and $\omega_m$ are nearly equal to each other because $\phi_1$ is unknown. However, if $\omega_s$ and $\omega_m$ are made to differ suitably from each other so that, in spectra in equation (26), envelope spectra centered on frequencies $\pm(\omega_s-\omega_m)$ may not overlap, the envelope can be determined. Even in such a case, a trigonometric function indicative of a carrier signal of the receiving signal remains and hence an additional detection processing is required after the processing by the digital adder 3.

The case where $\omega_s$ and $\tau_n$ are known and approximate value $\omega_m$ of $\omega_s$ and the time difference $\tau_n-\tau_1$ between the receiving signal of each element and the standard receiving signal are known has been described, but signal processings for cases where $\omega_s$ and the time difference $\tau_n-\tau_1$ between the receiving signal of each element and the standard receiving signal are known and where approximate value $\omega_m$ of $\omega_s$ and $\tau_n$ are known can be analogized easily from the present embodiment.

Third Embodiment

Figure 10:
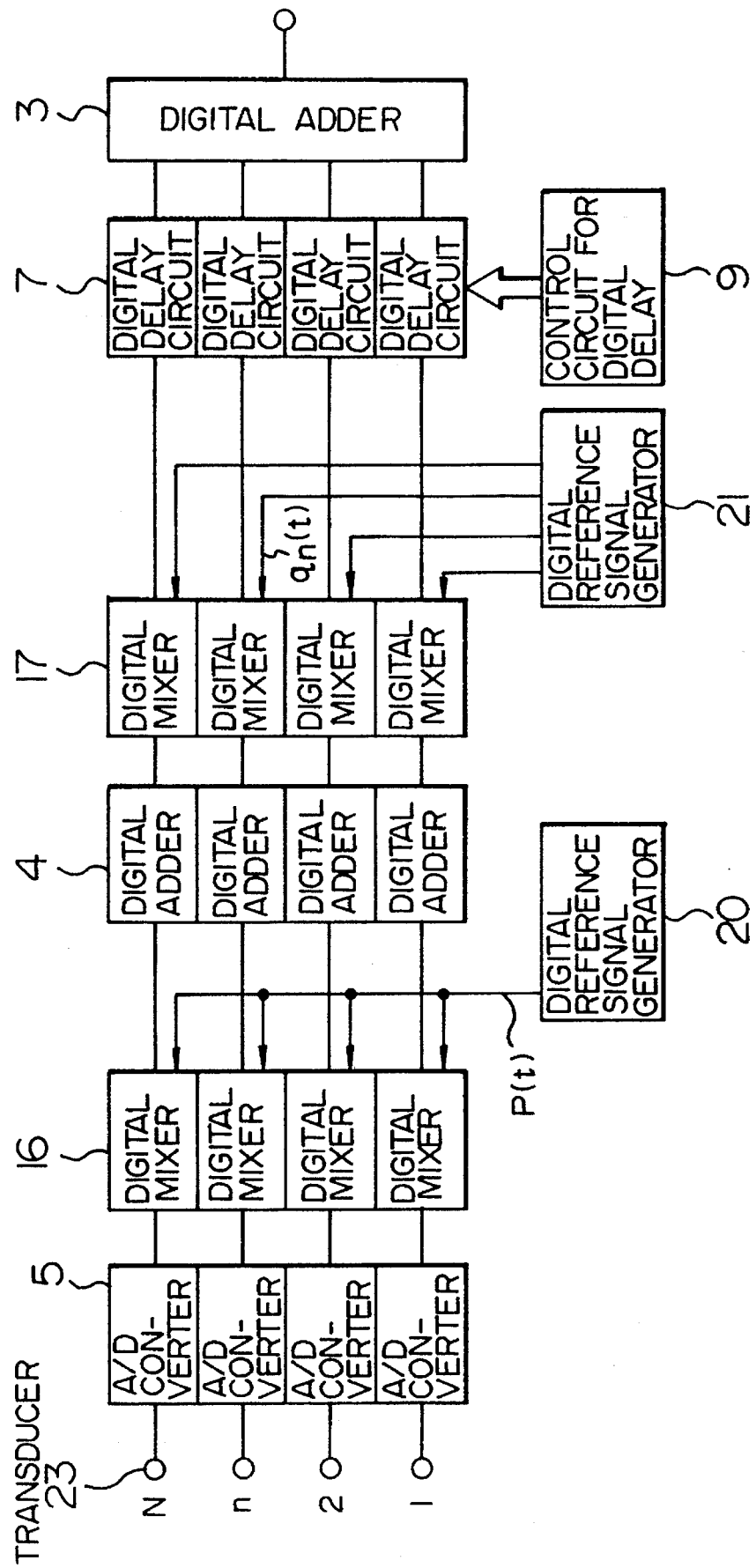
FIG. 10 is a diagram showing a configuration of an ultrasound signal processor according to a third embodiment of the present invention.

FIG. 10 is a diagram showing a configuration of an ultrasound signal processor according to a third embodiment of the present invention. The present embodiment is a further modification of the first embodiment shown in FIG. 1. Namely, the multiplication of equation (3) by $h_n(t)$ is decomposed as below $$h_n(t) = \exp\{-j(\omega_s t - \phi_n)\} \quad (27)$$
$$= \exp(-j\omega_s t)\exp(j\phi_n)$$

so as to be considered as two multiplying operations which permit a configuration as shown in FIG. 10. The decomposition of $h_n(t)$ into the two multiplying operations is allowed only when the h n (t) is a complex variable function. In FIG. 10, reference numerals 16 and 17 designate digital mixers for multiplication which substitute for that carried out by the digital mixer 15 in FIG. 1. Denoted by 20 and 21 are digital reference signal generators used during digital mixing at the digital mixers 16 and 17. A signal waveform p(t) used for initial digital mixing by the digital mixer 16 is common to the respective elements and is $$p(t)=\exp(-j\omega_s t) \quad (28).$$

In the digital mixer 17, multiplication by a digital reference signal (which is different for each element)

$$q_n(t)=\exp(j\phi_n) \quad (29)$$

generated from the digital reference signal generator 21 is effected to compensate mutual phase difference. In this configuration, by providing arrangements each composed of only the digital mixer 17 and ensuing components in parallel or performing a multiplexing processing, signals from a plurality of positions in an object to be tested can be received simultaneously.

Figure 11:
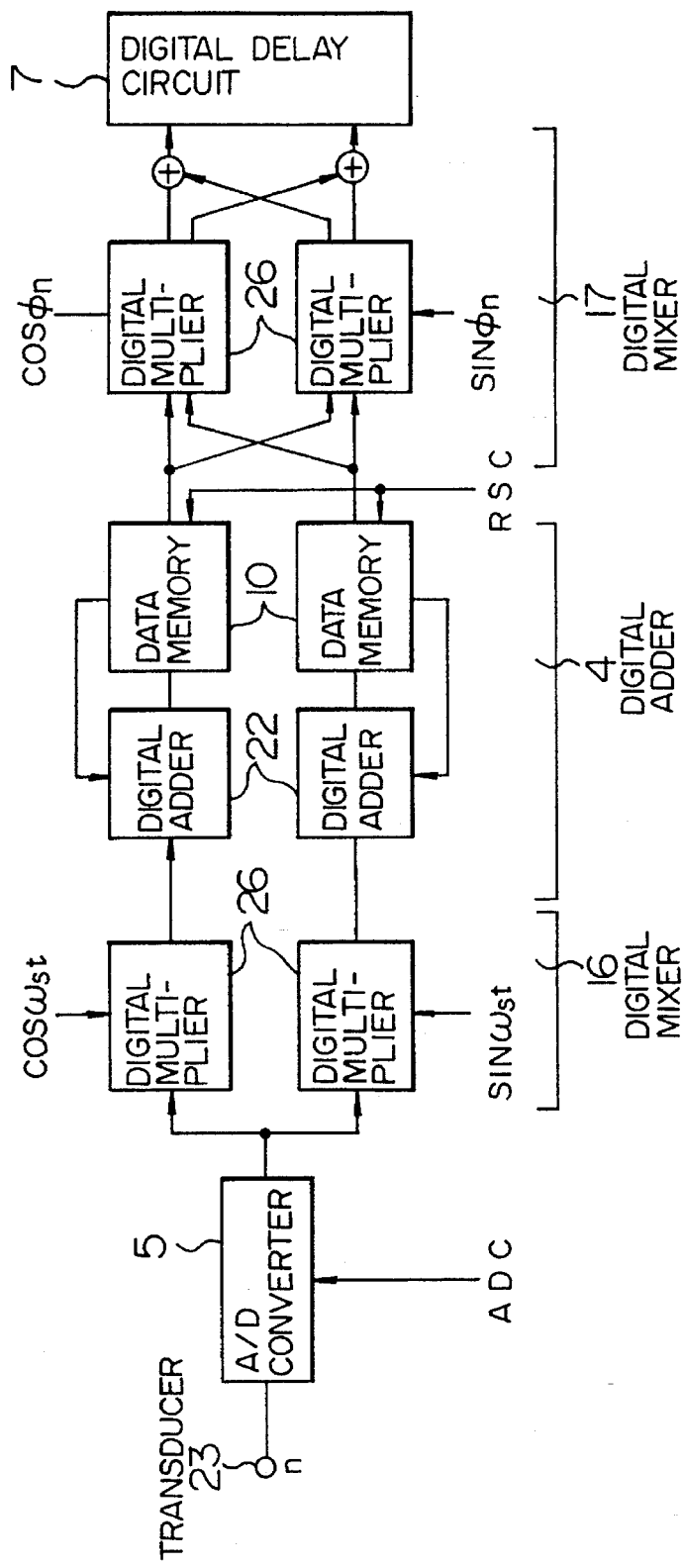
FIG. 11 is a diagram showing a configuration for processing of a single channel signal in the third embodiment of the present invention.
Figure 12:
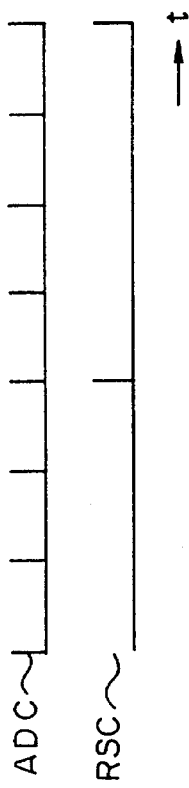
FIG. 12 is a diagram showing timing of a control signal in the third embodiment of the present invention.

FIG. 11 is a diagram showing a configuration for processing of a single channel signal in the third embodiment of the present invention. In FIG. 11, digital multipliers 26 corresponding to the digital mixers 16 and 17 in FIG. 10 use reference signals, 90° out of phase from each other, to perform multiplication. Digital mixer 17 multiplies complex output of digital adder 4 by complex digital reference signal exp(j$\phi_n$), and digital mixer 17 is composed of four elemental digital multipliers and two digital adders, for its figure being simplified 22 denotes digital adders for cumulation and 10 designates memories for temporary storage of results of addition at the digital adders 22 and which correspond to the digital adder 4 for cumulation addition in FIG. 10. The time relation between control signals is illustrated in FIG. 12. In the present embodiment, an analog to digital conversion (A/D conversion) command ADC and a command for ending cumulation and delivering results (cumulation/output) RSC are made to be synchronous with the transmitting signal to suppress noises. In FIG. 10, by changing, with time, control data generated by the digital reference signal generator 21 and the control circuit 9 for digital delay, the focal position can be shifted continuously.

Figure 13:
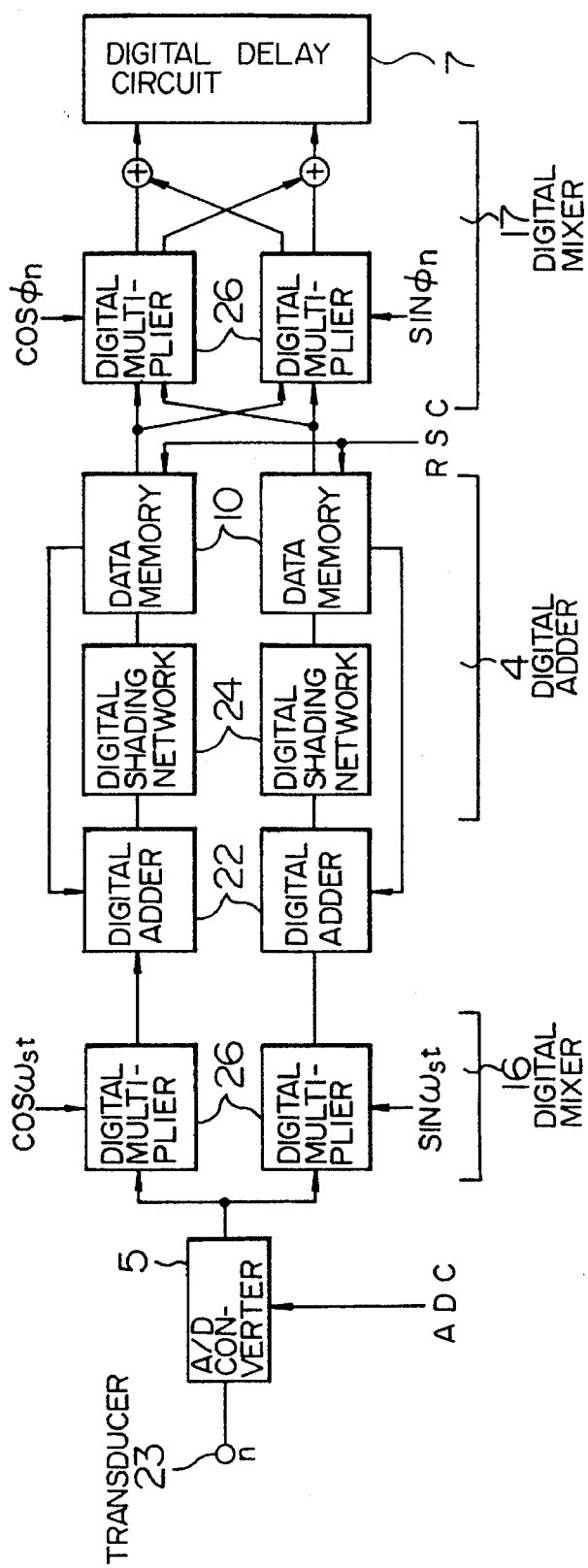
FIG. 13 is a diagram showing another configuration for processing of a single channel signal in the third embodiment of the present invention.
Figure 14:
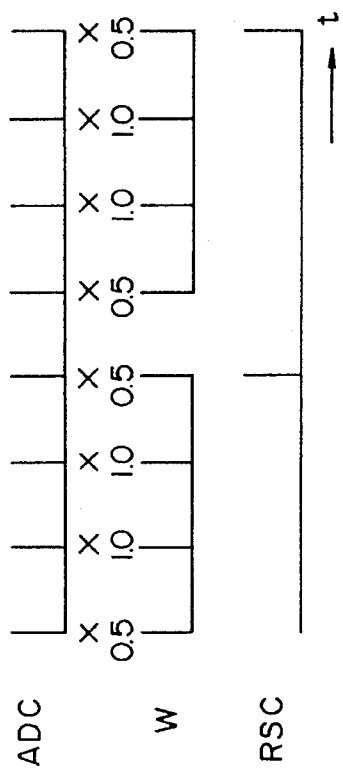
FIG. 14 is a diagram showing timing of a control signal in the third embodiment of the present invention.

FIG. 13 is a diagram showing another configuration for processing a single channel signal in the third embodiment of the present invention. In the present embodiment, digital shading networks 24 are interposed between the digital adders 22 for cumulation and the temporary memories 10 so that individual data pieces may be shaded differently during addition. Through this, the time relation among control signals (an analog to digital conversion (A/D conversion) command ADC, a command for ending cumulation and delivering results (cumulation/output) RSC and a digital shading generation command W) is set up as shown in FIG. 14 to ensure that digital data pieces individually shaded by the digital shading network 24 are added and delivered.

Fourth Embodiment

Figure 15:
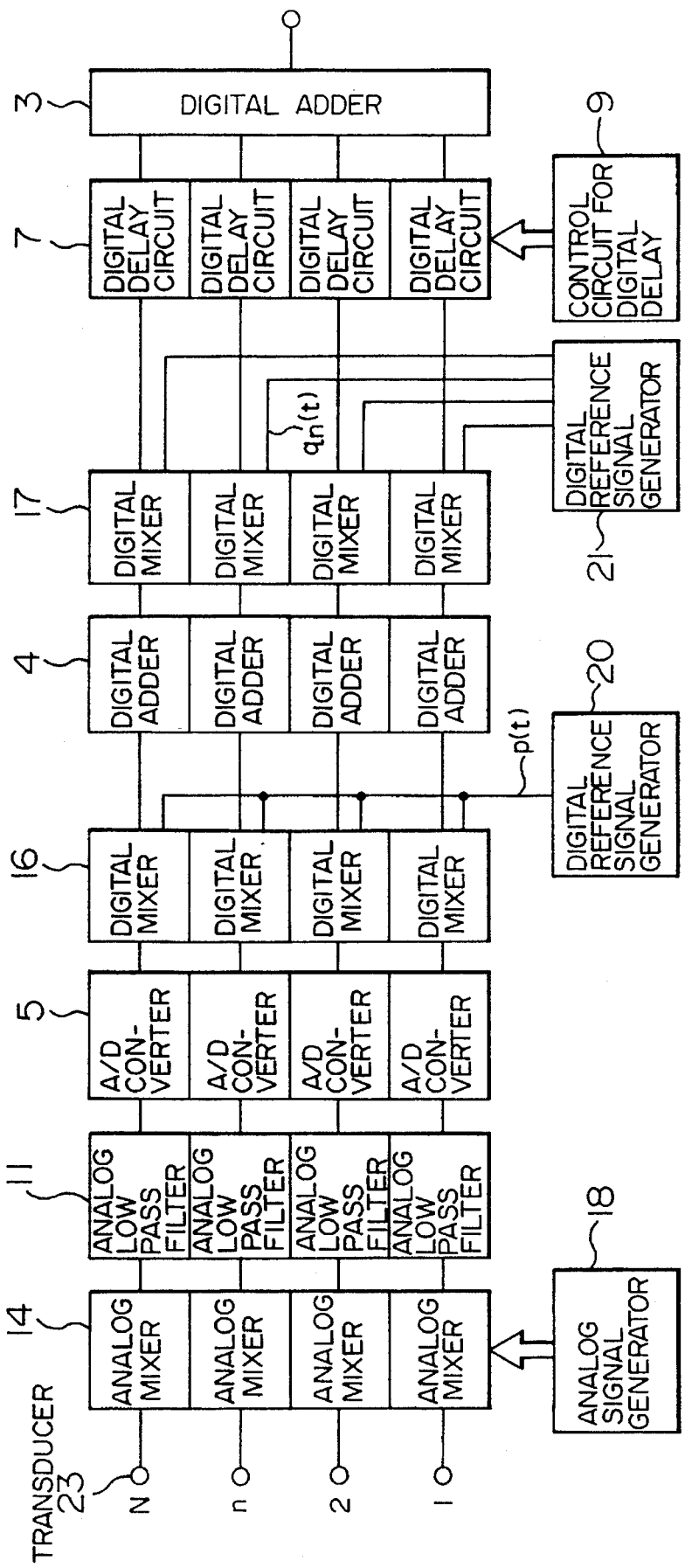
FIG. 15 is a diagram showing a configuration of an ultrasound signal processor according to a fourth embodiment of the present invention.

FIG. 15 is a diagram showing a configuration of an ultrasound signal processor according to a fourth embodiment of the present invention. The present embodiment is a further modification of the second embodiment shown in FIG. 8 and essentially, in the present embodiment, the configuration of the third embodiment shown in FIG. 10 is added with the analog mixer 14, analog reference signal generator 18 and analog low pass filter 11 shown in FIG. 8.

Figure 16:
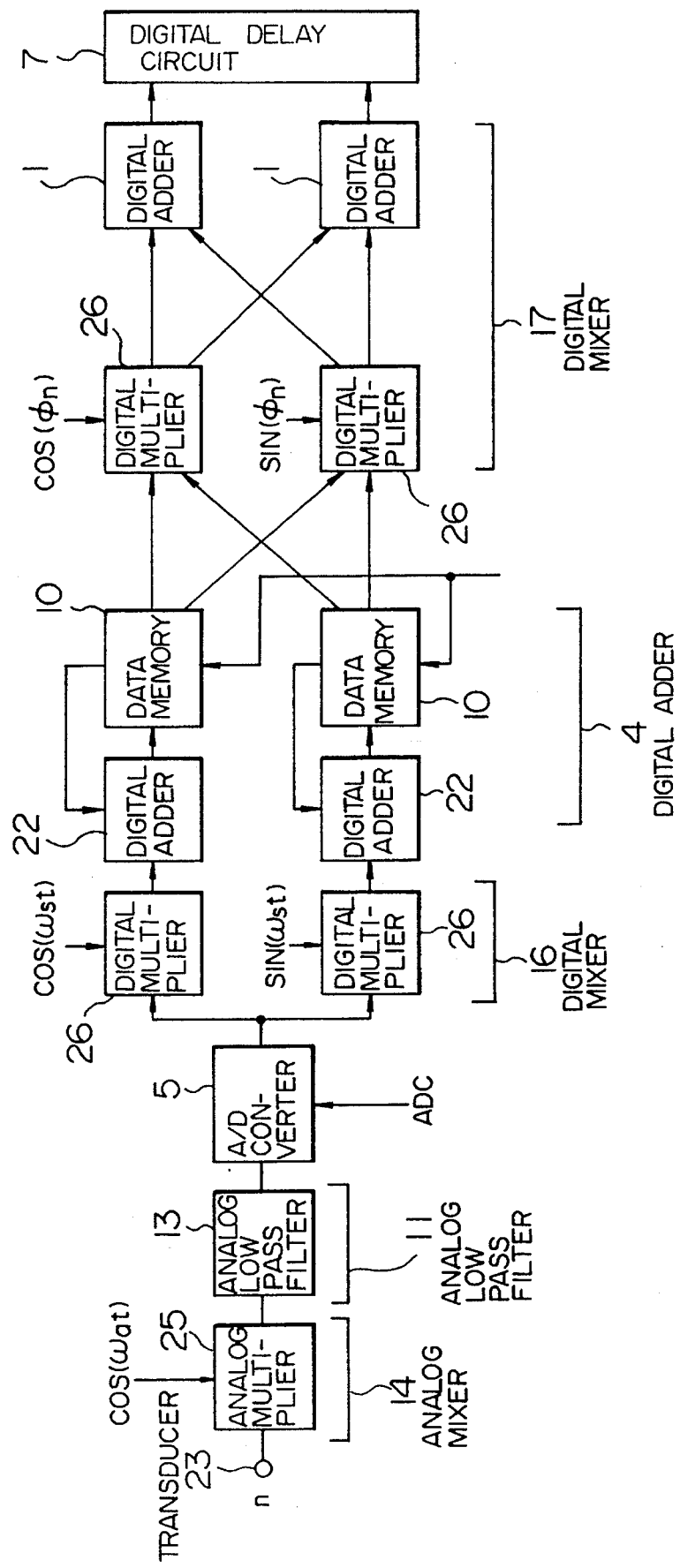
FIG. 16 is a diagram showing a configuration for processing of a single channel signal in the fourth embodiment of the present invention.

FIG. 16 is a diagram showing a configuration for processing of a single channel signal in the fourth embodiment of the present invention. In FIG. 16, an analog multiplier 25 corresponds to the analog mixer 14 in FIG. 15, an analog low pass filter 13 corresponds to the analog low pass filter 11 in FIG. 15, and digital multipliers 26 correspond to the digital mixers 16 and 17 in FIG. 15 and perform multiplication by using reference signals which are 90° out of phase from each other. 1 denotes digital adders for complex multiplication. 22 designates digital adders for cumulation and 10 denotes memories for temporary storage of addition results of the digital adders 22, the adders 22 and memories 10 corresponding to the digital adder 4 for cumulation addition of FIG. 15. Like the third embodiment, the time relation between control signals (ADS and RSC) is set up as shown in FIG. 12 and the ADC and RSC are made to be synchronous with the transmitting signal to suppress noises. Also, as in the case of the third embodiment, by changing, with time, control data pieces generated by the digital reference signal generator 21 and the control circuit 9 for digital delay, the focal position can be shifted continuously.

Figure 17:
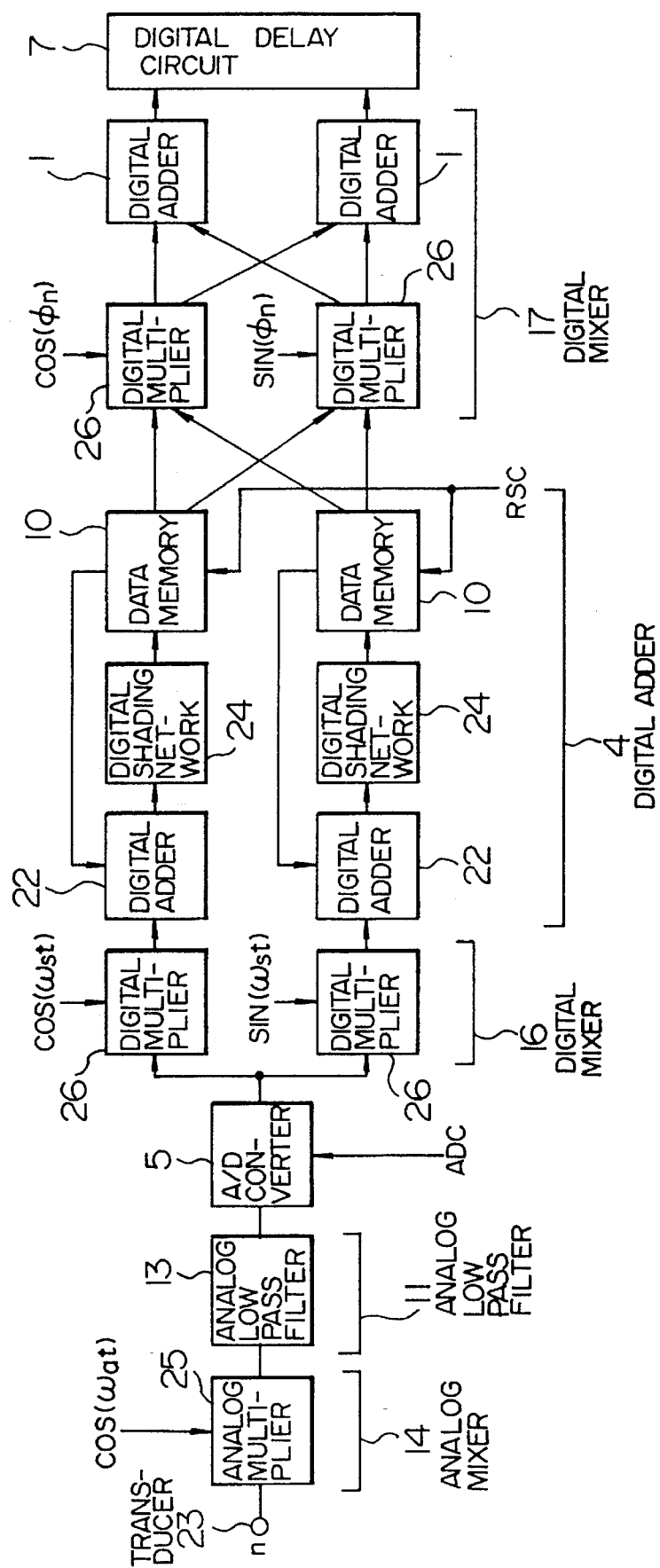
FIG. 17 is a diagram showing another configuration for processing of a single channel signal in the fourth embodiment of the present invention.

FIG. 17 is a diagram showing another configuration for processing of a single channel signal in the fourth embodiment of the present invention. In the present embodiment, like the configuration shown in FIG. 13, digital shading networks 24 are interposed between the digital adders 22 for cumulation and the temporary memories 10 so that individual data pieces may be shaded differently during addition. As in the case of FIG. 13, the time relation among control signals is set up as shown in FIG. 14 to ensure that digital data pieces individually shaded by the digital shading networks 24 are added and delivered.

Fifth Embodiment

Arrangements adapted to perform a processing of the digital mixer 17 and the ensuing processings shown in FIG. 13 are provided in parallel as will be described below.

Figure 18:
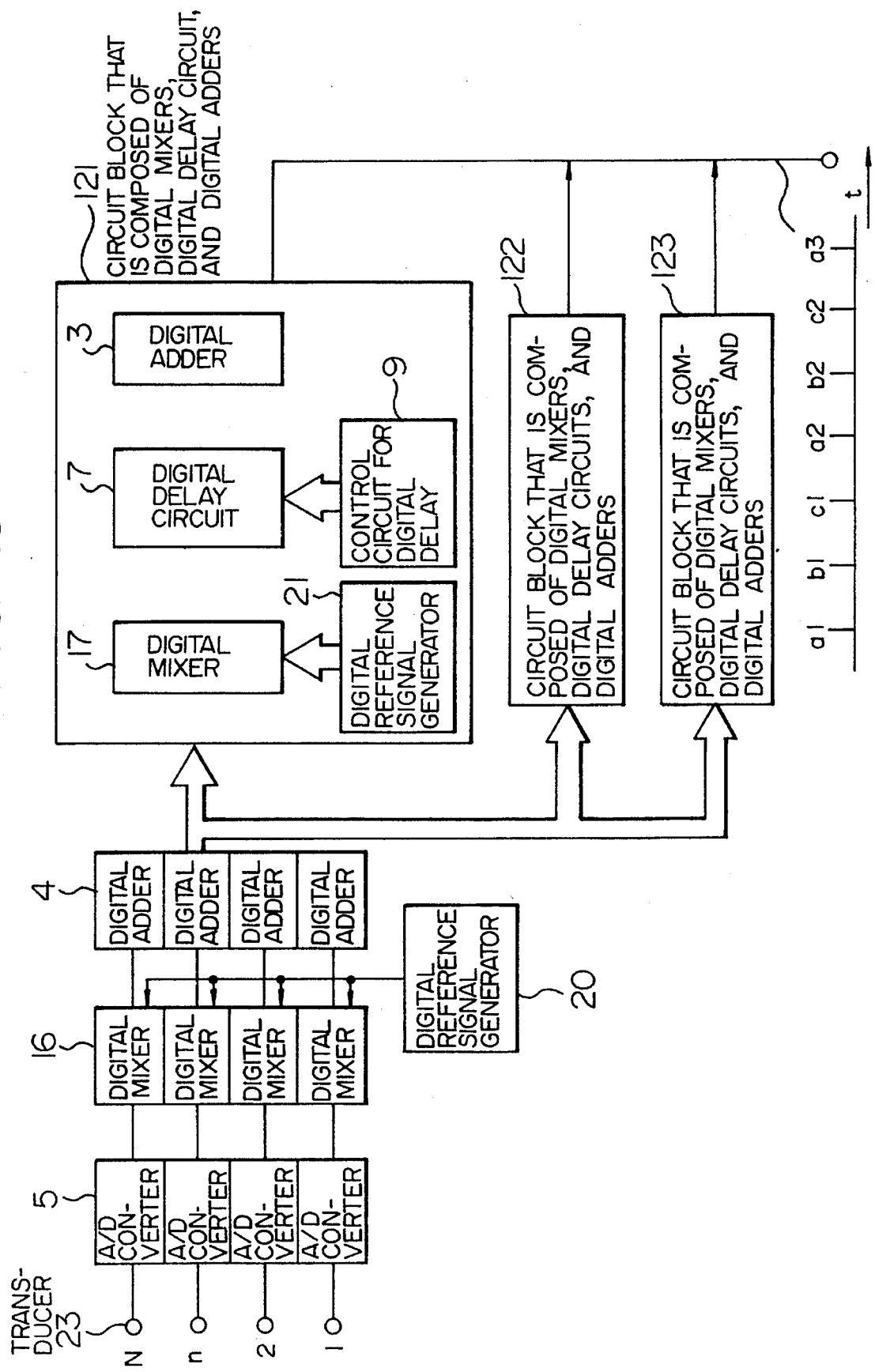
FIG. 18 is a diagram showing a configuration of an ultrasound signal processor according to a fifth embodiment of the present invention.

FIG. 18 is a diagram showing a configuration of an ultrasound signal processor according to a fifth embodiment of the present invention. In FIG. 18, reference numerals used in FIG. 10 designate like components and blocks 121 to 123 having each digital mixers 17, digital delay circuits 7 and digital adders 3 are connected in parallel. Denoted by $a_1$ to $a_3$ are outputs from the block 121, by $b_1$ and $b_2$ are outputs from the block 122 and by $c_1$ and $c_2$ are outputs from the block 123, the outputs indicating signal values corresponding to an ultrasound beam formed by each block. By providing the three delay/addition arrangements in parallel after the digital mixers 4 for cumulation, receiving beams in three different directions can be formed on time division basis.

Sixth Embodiment

Figure 19:
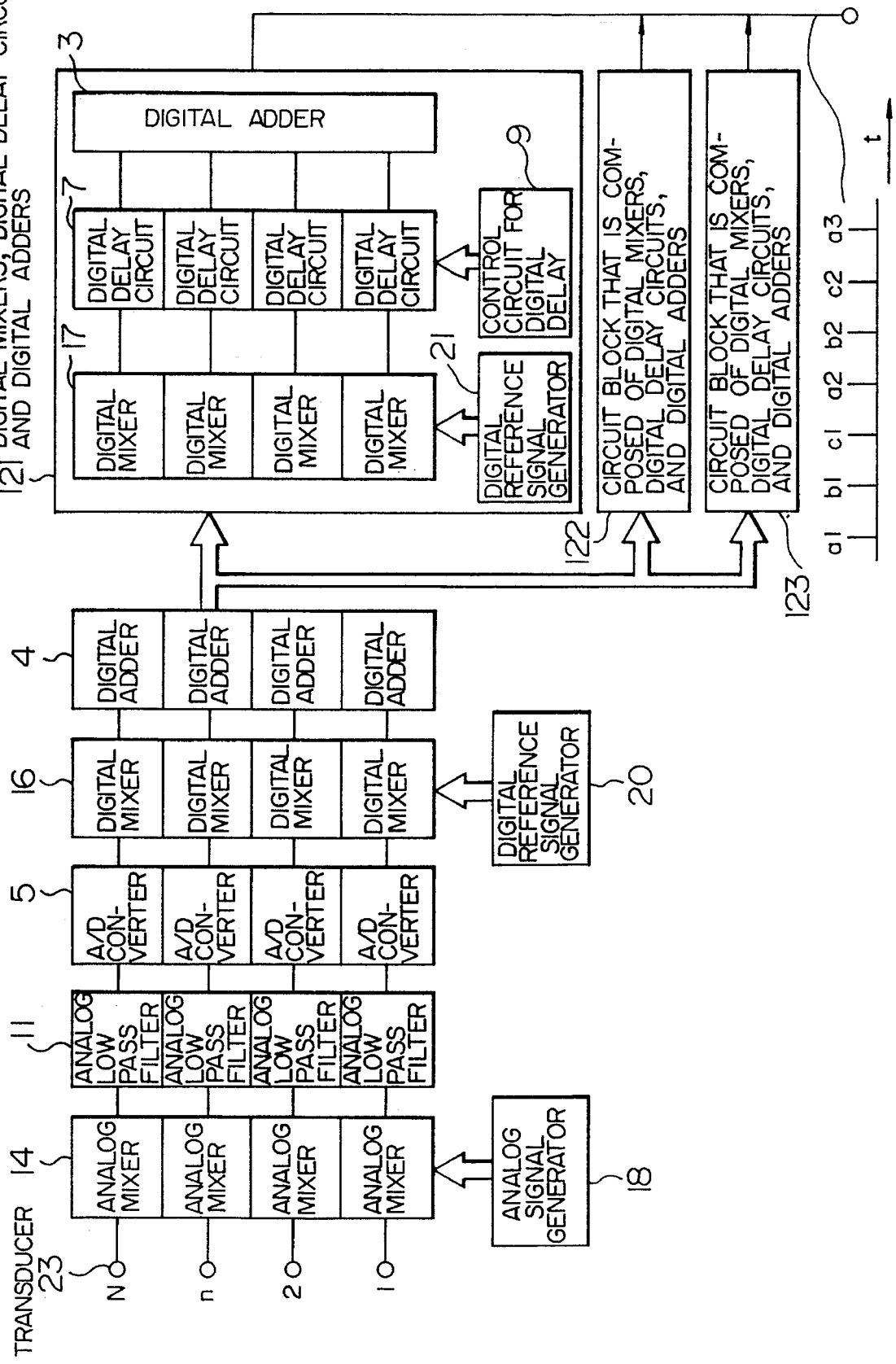
FIG. 19 is a diagram showing a configuration of an ultrasound signal processor according to a sixth embodiment of the present invention.

FIG. 19 is a diagram showing a configuration of an ultrasound signal processor according to a sixth embodiment of the present invention. Essentially, in the present embodiment, the analog mixer 14, analog reference signal generator 18 and analog low pass filter 11 shown in FIG. 8 are added to the configuration of the fifth embodiment shown in FIG. 18.

Seventh Embodiment

A configuration for storing all signals after the over-sampling processing to effect focus adjustment will now be described.

Figure 20:
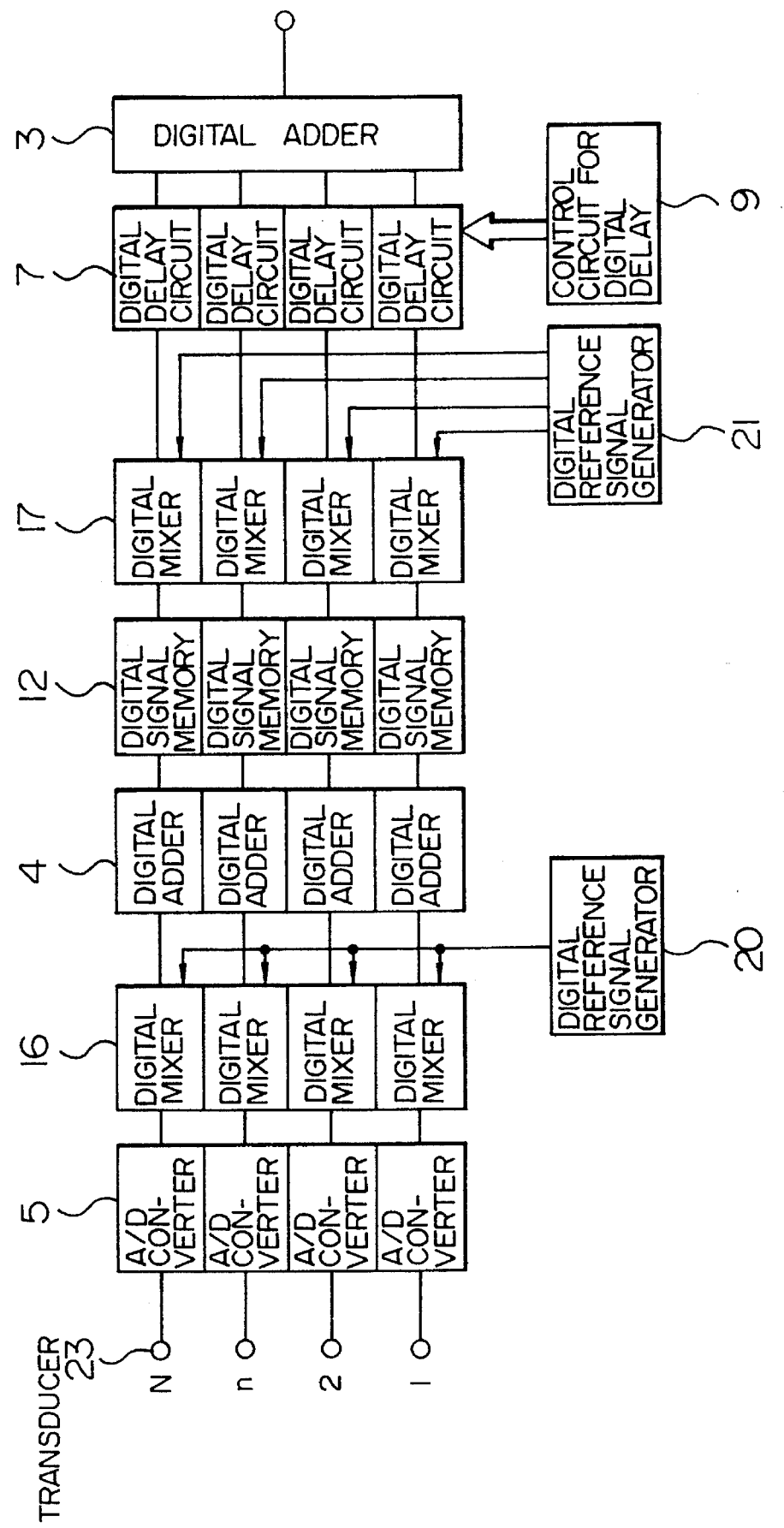
FIG. 20 is a diagram showing a configuration of an ultrasound signal processor according to a seventh embodiment of the present invention.

FIG. 20 is a diagram showing a configuration of an ultrasound signal processor according to a seventh embodiment of the present invention. In FIG. 20, digital signal memories 12 are interposed between digital adders 4 for cumulation and digital mixers 17. The memory is adapted to efficiently store data necessary for performing focus adjustment based on adaptive image reconstruction. A signal after the over-sampling processing preserves all information pieces within a band of a receiving signal which are caused by beat-down to be preserved within a low frequency band, and therefore the number of storing data pieces representative of the signal is compressed. By performing phase correction of the signal from the digital mixer 17 and time shift by the digital delay circuit 7 carried out in a complimentary manner to the phase correction, a beamforming method complying with conditions of an object to be imaged can be realized. Through this, delay time $\tau_n$ applied to one receiving element after another can be changed in expectation of the fact that, for example, the speed of sound sightly changes from one portion to another within an object to be tested.

Eighth Embodiment

Figure 21:
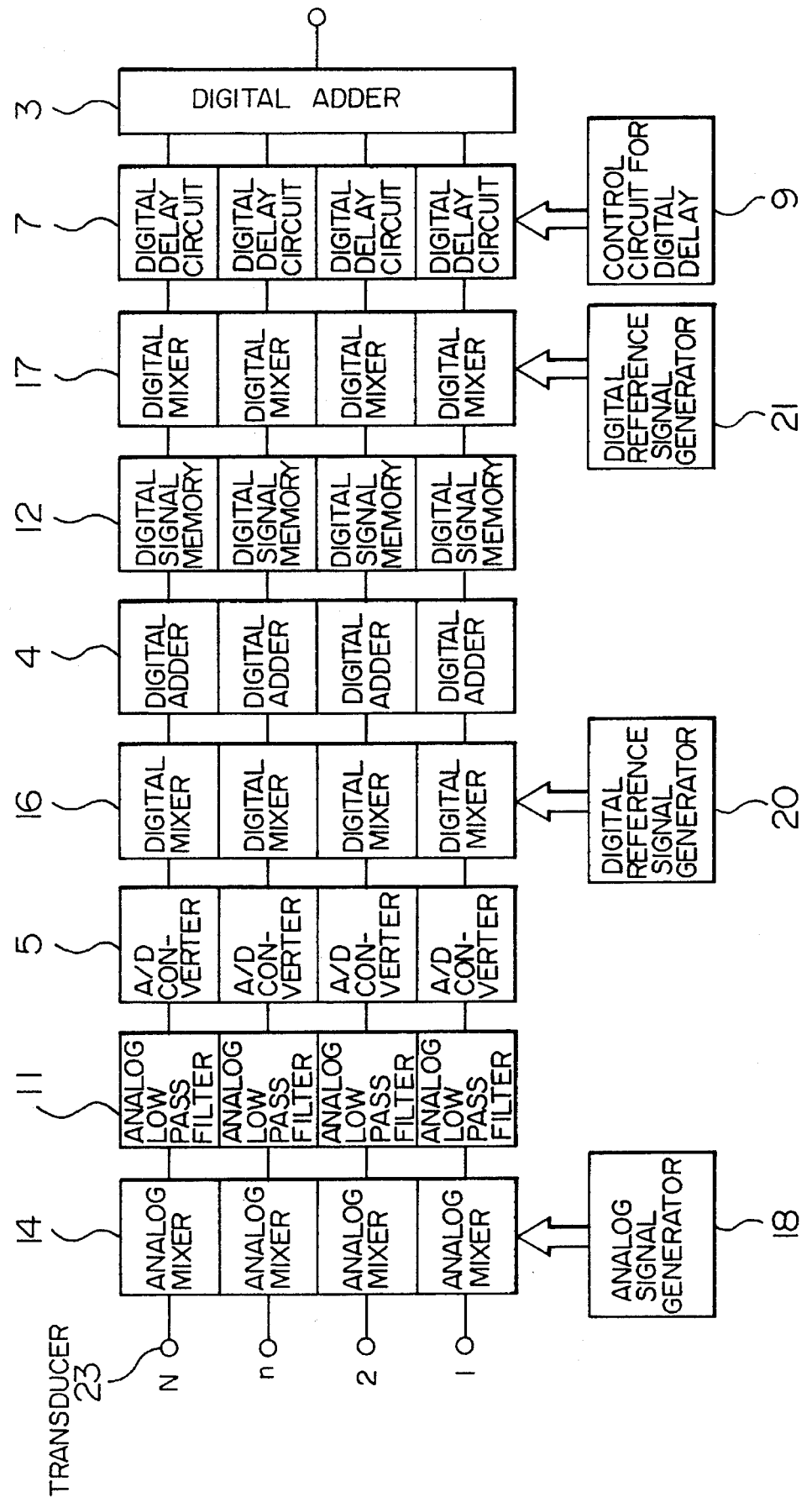
FIG. 21 is a diagram showing a configuration of an ultrasound signal processor according to an eighth embodiment of the present invention.

FIG. 21 is a diagram showing a configuration of an ultrasound signal processor according to an eighth embodiment of the present invention. Essentially, in the present embodiment, the analog mixer 14, analog reference signal generator 18 and analog low pass filter 11 are added to the configuration of the seventh embodiment shown in FIG. 20.

In the second, fourth, sixth and eighth embodiments described previously, the configuration of the analog to digital converter for handling an ultrasound signal having a higher center frequency than that in the first, third, fifth and seventh embodiments can be simplified.

In the respective embodiments described as above, the frequency of a receiving signal after the analog beat-down is made to be coincident with that of a digital reference signal but the present invention is in no way limited thereto and the frequency of the digital reference signal may be changed with time.

Figure 22:
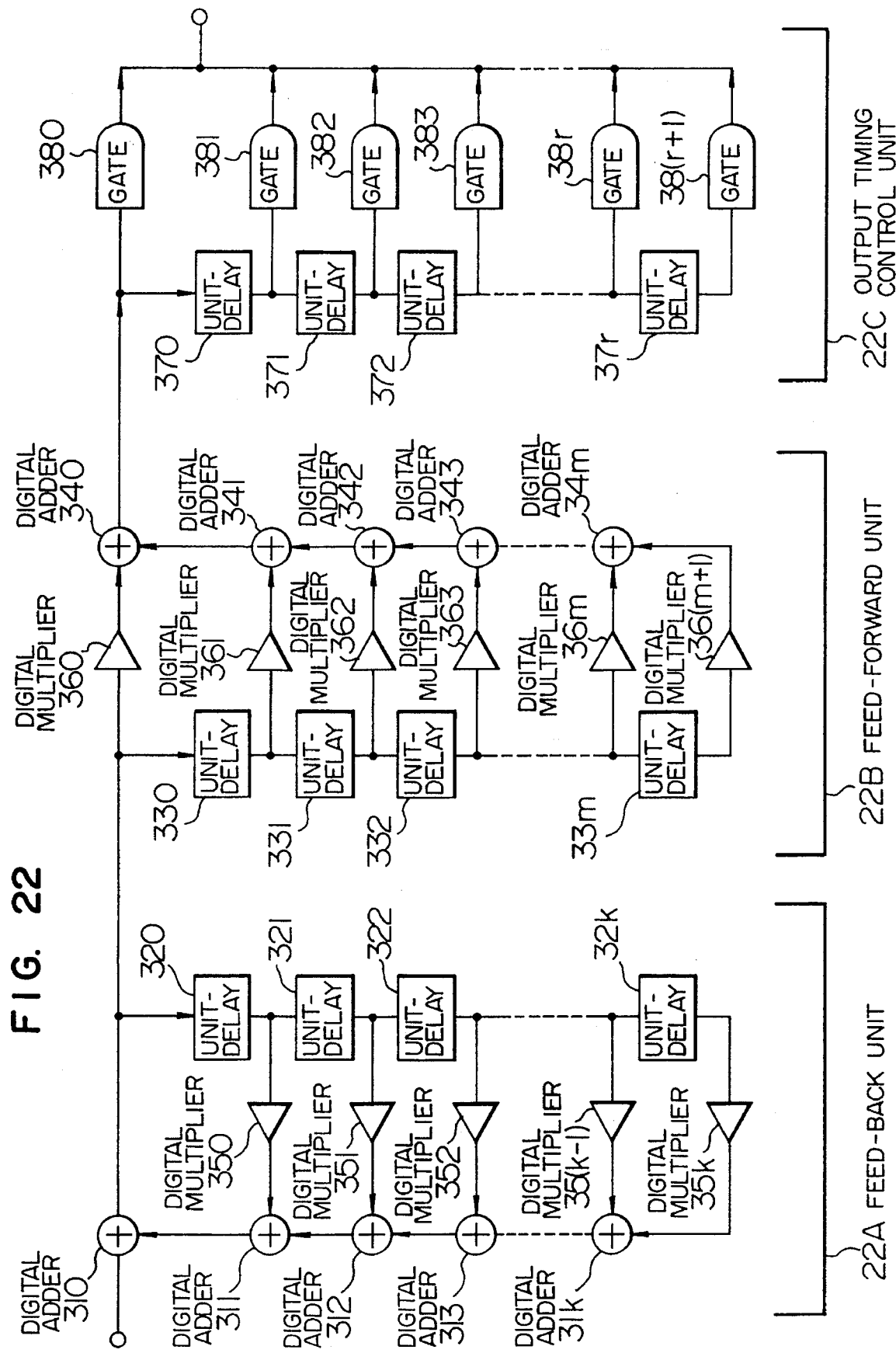
FIG. 22 is a diagram showing another configuration for realizing cumulation and addition in the respective embodiments of the present invention.

The configuration of the adder 4 for cumulation is not limited to that described previously and various configurations thereof may be conceivable provided that they have the integrating effect due to addition. For example, an arrangement as shown in FIG. 22 may be employed wherein shading necessary for individual data pieces can be realized at a high degree of freedom. In FIG. 22, reference numerals 310 to 31k and 340 to 34m designate adders, 320 to 32k, 330 to 33m and 370 to 37r designate unit-delay circuits, 350 to 35k and 360 to 36(m+1) designate multipliers and 380 to 38(r+1) designate gates. Coefficients of the respective multipliers may be fixed or may be read out of a memory, not shown, in compliance with purposes. Denoted by k, m and r are integers, not negative, which are determined by intended configuration and scale. With this configuration, by utilizing a feed-back unit 22A or a feed-forward unit 22B, an integrating circuit having a desired frequency characteristic can be set up. Further, the output frequency and timing offset can be controlled desirably by means of an output timing control unit 22C. The scale or the presence or absence of 22A, 22B and 22C is selected as necessary. Obviously, in addition to the illustrated configuration, many configurations having the same function as that of FIG. 22 may be available.

In the respective embodiments set forth so far, the arrangement of the digital delay circuit 7 and digital mixer 17 may be changed as necessary. In the foregoing embodiments, the absolute amplitude of the reference signal envelope in the analog mixer 14 and digital mixers 15, 16 and 17 is set to 1 (one) but this is not limitative and the amplitude of the reference signal envelope may be changed for each element to shade receiving signals. In the signal processor of the present invention, the cumulation processing after the beat-down of a receiving signal is realized and the over-sampling processing acts effectively to simplify the configuration of the analog to digital converter, and the present processor can therefore be applied to various apparatus in addition to the ultrasound apparatus. In the foregoing embodiments, each of the digital circuits such as the digital reference signal generator, digital delay circuit, control circuit for digital delay, digital adder and digital mixer may be constructed by using a corresponding analog circuit, an A/D converter and/or D/A converter in combination.

Many different embodiments of the present invention may be constructed without departing from the spirit and scope of the invention. It should be understood that the present invention is not limited to the specific embodiments described in this specification. To the contrary, the present invention is intended to cover various modifications and equivalent arrangements included within the spirit and scope of the claims.

What is claimed is:

1. An ultrasound signal processor having receiving means to receive a plurality of echo signals and visualize an object detected by using ultrasound signals, said ultrasound signal processor comprising:

digitizing means for digitizing a plurality of analog receiving signals from said receiving means;

waveform conversion means for converting signal waveforms by multiplying digital signals produced by said digitizing means by reference signals of predetermined frequencies;

cumulation means for performing cumulation processings of converted signals produced by said waveform conversion means;

delay means for delaying signals subjected to the cumulation processings by said cumulation means; and adder means for adding a plurality of signals delayed by said delay means;

wherein said waveform conversion means includes first and second waveform conversion means, an output terminal of said first conversion means is connected to an input terminal of said cumulation means, and a plurality of means, each comprising said second waveform conversion means, said delay means and said adder means, are connected in parallel to an output terminal of said cumulation means.

2. An ultrasound signal processor having receiving means to receive a plurality of echo signals and visualize an object detected by using ultrasound signals, said ultrasound signal processor comprising:

analog waveform conversion means for converting signal waveforms by multiplying a plurality of analog receiving signals from said receiving means by analog reference signals of predetermined frequencies;

filter means for passing low frequency components of converted signal waveforms produced by said analog waveform conversion means;

digitizing means for digitizing output signals of said filter means;

digital waveform conversion means for converting signal waveforms by multiplying digital signals produced by said digitizing means by reference signals of predetermined frequencies;

cumulation means for performing cumulation processings of converted signals converted by said digital waveform conversion means;

delay means for delaying signals subjected to the cumulation processings by said cumulation means; and adder means for adding a plurality of signals delayed by said delay means;

wherein said digital waveform conversion means includes first and second waveform conversion means, an output terminal of said first conversion means is connected to an input terminal of said cumulation means, and a plurality of means, each comprising said second waveform conversion means, said delay means and said adder means, are connected in parallel to an output terminal of said cumulation means.

3. An ultrasound signal processor having receiving means to receive a plurality of echo signals and visualize an object detected by using ultrasound signals, said ultrasound signal processor comprising:

analog waveform conversion means for converting signal waveforms by multiplying a plurality of analog receiving signals from said receiving means by analog reference signals of predetermined frequencies;

filter means for passing low frequency components of converted signal waveforms produced by said analog waveform conversion means;

digitizing means for digitizing output signals of said filter means;

digital waveform conversion means for converting signal waveforms by multiplying digital signals produced by said digitizing means by reference signals of predetermined frequencies;

cumulation means for performing cumulation processings of converted signals converted by said digital waveform conversion means;

delay means for delaying signals subjected to the cumulation processings by said cumulation means; and adder means for adding a plurality of signals delayed by said delay means;

wherein said cumulation means includes means for cumulating converted digital signals such that COUNT$\leq$(ADFQ/BW) stands, where BW is the bandwidth of an envelope for receiving signals represented by a low frequency component of the output of said digital waveform conversion means, ADFQ is the sampling frequency of said digitizing means, and COUNT is the number of cumulation operations.

4. An ultrasound signal processor having receiving means to receive a plurality of echo signals and visualize an object detected by using ultrasound signals, said ultrasound signal processor comprising:

analog waveform conversion means for converting signal waveforms by multiplying a plurality of analog receiving signals from said receiving means by analog reference signals of predetermined frequencies;

filter means for passing low frequency components of converted signal waveforms produced by said analog waveform conversion means;

digitizing means for digitizing output signals of said filter means;

digital waveform conversion means for converting signal waveforms by multiplying digital signals produced by said digitizing means by reference signals of predetermined frequencies;

cumulation means for performing cumulation processings of converted signals converted by said digital waveform conversion means;

delay means for delaying signals subjected to the cumulation processings by said cumulation means; and adder means for adding a plurality of signals delayed by said delay means;

wherein said analog waveform conversion means includes means for multiplying said reference signal and said receiving signal which are set such that $\omega_a \leq \omega_s - (BW/2)$ stands, wherein $\omega_a$ is the frequency of said reference signal, $\omega_s$ is the center frequency of said receiving signal and BW is the bandwidth for a transmitting signal represented by a low frequency component of the output of said digital waveform conversion means.

5. An ultrasonic signal processor having receiving means which include a plurality of elements to receive a plurality of echo signals from an object to be tested and visualize the object detected by using ultrasound signals, said ultrasonic signal processor comprising:

digitizing means for digitizing an analog echo signal received by said elements in a predetermined digitizing period, to obtain digital signals expressing a waveform of the received signals in digital form;

first digital waveform conversion means for converting the waveform of the digital signals by multiplying the digital signals produced from said digitizing means by digital reference signals with a predetermined frequency;

cumulation means for cumulating signals converted by said first digital waveform conversion means in a time period longer than the predetermined digitizing period;

second digital waveform conversion means for correcting a phase of the converted signals cumulated by said cumulation means;

delay means for delaying the signals corrected by said second digital waveform conversion means; and adder means for adding a plurality of delayed signals delayed by said delay means, each of the delayed signals being converted from an analog echo signal produced by each of said elements, wherein a plurality of circuit means, each including said second digital waveform conversion means, said delay means and said adder means are connected in parallel to an output terminal of said cumulation means.

6. An ultrasonic signal processor having receiving means which include a plurality of elements to receive a plurality of echo signals from an object to be tested and visualize the object detected by using ultrasound signals, said ultrasonic signal processor comprising:

digitizing means for digitizing an analog echo signal received by said elements in a predetermined digitizing period, to obtain digital signals expressing a waveform of the received signals in digital form;

first digital waveform conversion means for converting the waveform of the digital signals by multiplying the digital signals produced by said digitizing means by digital reference signals having a predetermined frequency;

cumulation means for cumulating the signals converted by said first digital waveform conversion means in a time period longer than the predetermined digitizing period;

second digital waveform conversion means for correcting a phase of the signals cumulated by said cumulation means;

delay means for delaying the signals corrected by said second digital waveform conversion means; and adder means for adding a plurality of delayed signals delayed by said delay means, each of the delayed signals being converted from an analog echo signal produced by each of said elements, wherein said cumulation means includes means for cumulating converted digital signals such that COUNT$\leq$(ADFQ/BW) stands, wherein BW is the bandwidth of an envelope for receiving signals represented by a low frequency component of the output of said first digital waveform conversion means, ADFQ is the sampling frequency of said digitizing means and COUNT is the number of cumulation operations.

7. An ultrasonic signal processor according to either of claim 5 or claim 6, wherein said digital reference signals are digital complex reference signals.

8. An ultrasonic signal processor according to either of claim 5 or claim 6, further comprising memory means for storing output signals of said cumulation means, and said second digital waveform conversion means reads out signals from said memory means.

9. An ultrasonic signal processor according to claim 5, wherein said cumulation means includes means for cumulating converted digital signals such that COUNT$\leq$(ADFQ/BW) stands, wherein BW is the bandwidth of an envelope for receiving signals represented by a low frequency component of the output of said first digital waveform conversion means, ADFQ is the sampling frequency of said digitizing means and COUNT is the number of cumulation operations.

10. An ultrasonic signal processor having receiving means which include a plurality of elements to receive a plurality of echo signals from an object to be tested and visualize the object detected by using ultrasound signals, said ultrasonic signal processor comprising:

analog waveform conversion means for converting a waveform of an echo signal received by said elements by multiplying the echo signal by an analog reference signal having a predetermined frequency;

filter means for passing low frequency components of converted signal waveforms by said analog waveform conversion means;

digitizing means for digitizing the output signal of said filter means in a predetermined digitizing period, to obtain digital signals expressing the waveforms of the received signals and digital form;

first digital waveform conversion means for converting the waveform of the digital signals by multiplying the digital signal produced by said digitizing means by digital reference signals having a predetermined frequency;

cumulation means for cumulating signals converted by said first digital waveform conversion means in a time period longer than the predetermined digitizing period;

second digital waveform conversion means for correcting a phase of the signals cumulated by said cumulation means;

delay means for delaying the signal corrected by said second digital waveform conversion means; and adder means for adding a plurality of delayed signals delayed by said delay means, each of the delayed signals being converted from an analog echo signal produced by each of said elements, wherein a plurality of circuit means, each comprising said second digital waveform conversion means, said delay means and said adder means, are connected in parallel to an output terminal of said cumulation means.

11. An ultrasonic signal processor having receiving means which include a plurality of elements to receive a plurality of echo signals from an object to be tested and visualize the object detected by using ultrasound signals, said ultrasonic signal processor comprising:

analog waveform conversion means for converting a waveform of an echo signal received by said elements by multiplying the echo signal by an analog reference signal having a predetermined frequency;

filter means for passing low frequency components of a signal waveform converted by said analog waveform conversion means;

digitizing means for digitizing the output signal of said filter means in a predetermined digitizing period, to obtain digital signals expressing a waveform of the received signals in digital form;

first digital waveform conversion means for converting the waveform of the digital signals by multiplying the digital signal produced by said digitizing means by digital reference signals having a predetermined frequency;

cumulation means for cumulating signals converted by said first digital waveform conversion means in a time period longer than the predetermined digitizing period;

second digital waveform conversion means for correcting a phase of the signals cumulated by said cumulation means;

delay means for delaying the signals corrected by said second digital waveform conversion means; and adder means for adding a plurality of delayed signals delayed by said delay means, each of the delayed signals being converted from an analog echo signal produced by each of said elements;

wherein said cumulation means includes means for cumulating converted digital signals such that COUNT$\leq$(ADFQ/BW) stands, wherein BW is the bandwidth of an envelope for receiving signals represented by a low frequency component of the output of said first digital waveform conversion means, ADFQ is a sampling frequency of said digitizing means and COUNT is the number of cumulation operations.

12. An ultrasonic signal processor having receiving means which include a plurality of elements to receive a plurality of echo signals from an object to be tested and visualize the object detected by using ultrasound signals, said ultrasonic signal processor comprising:

analog waveform conversion means for converting a waveform of an echo signal received by said elements by multiplying the echo signal by an analog reference signal having a predetermined frequency;

filter means for passing low frequency components of the signal waveform converted by said analog waveform conversion means;

digitizing means for digitizing the output signal of said filter means in a predetermined digitizing period to obtain digital signals expressing the waveform of the received signals in digital form;

first digital waveform conversion means for converting the waveform of the digital signals by multiplying the digital signals produced by said digitizing means by digital reference signals having a predetermined frequency;

cumulation means for cumulating signals converted by said first digital waveform conversion means in a time period longer than the predetermined digitizing period;

second digital waveform conversion means for correcting a phase of the signals cumulated by said cumulating means;

delay means for delaying the signals corrected by said second digital waveform conversion means; and adder means for adding a plurality of delayed signals delayed by said delay means, each of the delayed signals being converted from an analog echo signal produced by each of said elements;

wherein said analog waveform conversion means includes means for multiplying said digital reference signal and said received signals so that $\omega_a \leq \omega_s - (BW/2)$ stands, wherein $\omega_a$ is the predetermined frequency of said digital reference signal, $\omega_s$ is the frequency of the received signal and BW is the bandwidth of an envelope for receiving signals represented by a low frequency component of the output of said first digital waveform conversion means.

13. An ultrasonic signal processor according to any one of claims 10–12, wherein said digital reference signals are digital complex reference signals.

14. An ultrasonic signal processor according to any one of claims 10–12, further comprising memory means for storing output signals of said cumulation means, and said second digital waveform conversion means reads out signals from said memory means.

15. An ultrasonic signal processor according to claim 13 further comprising memory means for storing output signals of said cumulation means, and said second digital waveform conversion means reads out signals from said memory means.

* * * * *